US009801865B2

(12) United States Patent
Moran

(10) Patent No.: US 9,801,865 B2
(45) Date of Patent: Oct. 31, 2017

(54) MATERIALS AND METHODS FOR DIAGNOSIS, PREVENTION AND/OR TREATMENT OF STRESS DISORDERS AND CONDITIONS ASSOCIATED WITH ABETA PEPTIDE AGGREGATION

(75) Inventor: Valentina Echeverria Moran, Largo, FL (US)

(73) Assignees: The United States of America as represented by the Department of Veteran Affairs, Washington, DC (US); University of South Florida, Tampa, FL (US)

( * ) Notice: Subject to any disclaimer, the term of this patent is extended or adjusted under 35 U.S.C. 154(b) by 146 days.

(21) Appl. No.: 12/586,681

(22) Filed: Sep. 24, 2009

(65) Prior Publication Data

US 2010/0104504 A1    Apr. 29, 2010

Related U.S. Application Data

(60) Provisional application No. 61/194,064, filed on Sep. 24, 2008, provisional application No. 61/099,746, filed on Sep. 24, 2008.

(51) Int. Cl.
*A61K 31/4439* (2006.01)
*A61K 51/04* (2006.01)
*C07D 401/04* (2006.01)

(52) U.S. Cl.
CPC ...... *A61K 31/4439* (2013.01); *A61K 51/0455* (2013.01); *C07D 401/04* (2013.01)

(58) Field of Classification Search
CPC ............ A61K 31/4439; A61K 51/0455; C07D 401/04
USPC ...................................................... 424/1.11
See application file for complete search history.

(56) References Cited

U.S. PATENT DOCUMENTS

| 3,870,794 | A | * | 3/1975 | Hutchinson et al. ......... 514/343 |
| 4,938,949 | A | | 7/1990 | Borch et al. |
| 5,187,169 | A | * | 2/1993 | Lippiello et al. ............. 514/343 |
| 5,612,357 | A | * | 3/1997 | Keenan et al. ............... 514/343 |
| 2003/0166554 | A1* | | 9/2003 | Cohen et al. .................... 514/12 |
| 2004/0223909 | A1* | | 11/2004 | Montalto et al. ............ 424/1.11 |
| 2004/0242698 | A1* | | 12/2004 | Hughes ........................... 514/618 |
| 2007/0066665 | A1* | | 3/2007 | Yang et al. ..................... 514/367 |
| 2010/0234349 | A1* | | 9/2010 | Olsen et al. ............. 514/211.13 |

FOREIGN PATENT DOCUMENTS

WO    WO 2008103818 A1 *  8/2008

OTHER PUBLICATIONS

Halldin et al. Nucl. Med. Biol., 1992, 871-880.*
Yeng et al. J Biol Chem. 2005, 5892-5901.*
Zeng et al. Biol. Psychiatry 2001, 248-257.*
Hamada et al. J Pharm. Exp. Therap. 315: 872-878, 2005.*
Vainio et al. Nic. Tobac. Research (2001) 3, 177-182.*
Court et al. Biol Psychiatry 2001; 49: 175-184.*
Milad et al. Biol. Psychology 73 (2006) 61-71.*
Quirk et al. Biol. Psychiatry 2006; 60: 337-343.*
Kalaitzakis et al. J. Neuropathol Exp. Neurol. 2008, 67, 155-161.*
Berendsen, HJC. et al. "GROMACS: A message-passing parallel molecular dynamics implementation", 1995, *Computer Physics Communications*, pp. 43-56, vol. 91.
Boscarino, JE. "Posttraumatic stress disorder and mortality among U.S. Army veterans 30 years after military service", *Annals of Epidemiology*, 2006, pp. 248-56, vol. 16(4).
Briggs, CA. et al., "Human alpha 7 nicotinic acetylcholine receptor responses to novel ligands", *Neuropharmacology*, 1995, pp. 583-590, vol. 34.
Buccafusco, JJ. et al., "Disconnection between activation and desensitization of autonomic nicotinic receptors by nicotine and cotinine", *Neuroscience Letters*, 2007, pp. 68-71, vol. 413.
Calhoun, PS. et al., "Medical service utilization by veterans seeking help for posttraumatic stress disorder", *American Journal of Psychiatry*, 2002, pp. 2081-2086, vol. 159 (12).
Chromy, BA. et al., "Self-assembly of Abeta(1-42) into globular neurotoxins", *Biochemistry*, 2003, pp. 12749-12760, vol. 42.
Court, JA. et al., "Attenuation of Abeta deposition in the entorhinal cortex of normal elderly individuals associated with tobacco smoking", *Neuropathology & Applied Neurobiology*, 2005, pp. 522-535, vol. 31.
Daura, X. et al., "Folding-unfolding thermodynamics of a beta-heptapeptide from equilibrium simulations", *Proteins*, 1999, pp. 269-280, vol. 34.
Echeverria, V. et al., "Intracellular A-beta amyloid, a sign for worse things to come?", *Molecular Neurobiology*, 2002, 26(2-3):299-316.
Echeverria, V. et al., "Stimulation of PGE receptors EP2 and EP4 protects cultured neurons against oxidative stress and cell death following beta-amyloid exposure", *European Journal of Neuroscience*, 2005, pp. 2199-2206, vol. 22.

(Continued)

*Primary Examiner* — Michael G Hartley
*Assistant Examiner* — Sean R Donohue
(74) *Attorney, Agent, or Firm* — Adriano & Associates

(57) ABSTRACT

The subject invention concerns materials and methods for treating and/or preventing diseases associated with accumulation of Aβ peptide in neural tissue. The subject invention also concerns materials and methods for treating and/or preventing stress disorders, such as post-traumatic stress disorder (PTSD). In one embodiment, a method of the invention comprises administering a therapeutically effective amount of cotinine, or a pharmaceutically acceptable salt thereof, to a person or animal in need of treatment. The methods of the invention can be used to prevent and/or treat Alzheimer's disease and Parkinson's disease. The subject invention also concerns compositions that comprise cotinine, or a pharmaceutically acceptable salt thereof, and a pharmaceutically acceptable carrier, diluent or adjuvant. The subject invention concerns materials and methods for detecting and diagnosing conditions associated with accumulation of Aβ peptide in neural tissue, such as Alzheimer's disease and Parkinson's disease, using the chemical cotinine.

1 Claim, 25 Drawing Sheets

(56) References Cited

OTHER PUBLICATIONS

Gahring, LC. et al., "Nicotine-induced neuroprotection against N-methyl-D-aspartic acid or beta-amyloid peptide occur through independent mechanisms distinguished by pro-inflammatory cytokines", *Journal of Neurochemistry*, 2003, pp. 1125-1136, vol. 87.

Gallinat, J. et al., "Smoking and structural brain deficits: a volumetric MR investigation", *European Journal of Neuroscience*, 2006, pp. 1744-1750, vol. 24.

Hammond, DK. et al., "Metabolism of nicotine by rat liver cytochromes P-450. Assessment utilizing monoclonal antibodies to nicotine and cotinine", *Drug Metabolism & Disposition*, 1991, pp. 804-808, vol. 19.

Hellstrom-Lindahl, E. et al., "Nicotine reduces A beta in the brain and cerebral vessels of APPsw mice", *European Journal of Neuroscience*, 2004, pp. 2703-2710, vol. 19.

Hess, B. et al., "LINCS: A linear constraint solver for molecular simulations", *Journal of Computational Chemistry*, 1997, pp. 1463-1472, vol. 18.

Hoge, CW. et al., "Combat duty in Iraq and Afghanistan, mental health problems, and barriers to care", *New England Journal of Medicine*, 2004, pp. 13-22, vol. 351.

Hong, DP. et al., "Smoking and Parkinson's disease: does nicotine affect alpha-synuclein fibrillation?" *Biochimica et Biophysica Acta*, 2009, pp. 282-290, vol. 1794.

Hsiao, K. et al., "Correlative memory deficits, Abeta elevation, and amyloid plaques in transgenic mice", *Science*, 1996, pp. 99-102, vol. 274.

Kessler, RC. "Posttraumatic stress disorder: the burden to the individual and to society", *Journal of Clinical Psychiatry*, 2000, pp. 4-12, vol. 61(Suppl 5); discussion 13-4.

Kessler, RC. et al., "Prevalence, severity, and comorbidity of 12-month DSM-IV disorders in the National Comorbidity Survey Replication", *Archives of General Psychiatry*, 2005, pp. 617-627, vol. 62.

Kirschner, DA. et al., "Fiber diffraction as a screen for amyloid inhibitors", *Current Alzheimer Research*, 2008, pp. 288-307, vol. 5.

Kudo, Y. et al., "2-(2-[2-Dimethylaminothiazol-5-yl]ethenyl)-6-(2-[fluoro]ethoxy)benzoxazole: a novel PET agent for in vivo detection of dense amyloid plaques in Alzheimer's disease patients", *Journal of Nuclear Medicine*, 2007, pp. 553-561, vol. 48.

Levin, ED. "Nicotinic receptor subtypes and cognitive function", *Journal of Neurobiology*, 2002, pp. 633-640, vol. 53.

Lindahl, E. et al., "GROMACS 3.0: a package for molecular simulation and trajectory analysis", *Journal of Molecular Modeling*, 2001, pp. 306-317, vol. 7.

Merchant, C. et al., "The influence of smoking on the risk of Alzheimer's disease", *Neurology*, 1999, pp. 1408-1412, vol. 52.

Moore, SA. et al., "Both the D-(+) and L-(−) enantiomers of nicotine inhibit Abeta aggregation and cytotoxicity", *Biochemistry*, 2004, pp. 819-826, vol. 43.

Morris, GM. et al., "Automated Docking Using a Lamarckian Genetic Algorithm and Empirical Binding Free Energy Function", *Journal of Computational Chemistry*, 1998, pp. 1639-1662, vol. 19.

Necula M. et al., "Small molecule inhibitors of aggregation indicate that amyloid beta oligomerization and fibrillization pathways are independent and distinct", *Journal of Biological Chemistry*, 2007, pp. 10311-10324, vol. 282.

Nordberg, A. et al., "Chronic nicotine treatment reduces beta-amyloidosis in the brain of a mouse model of Alzheimer's disease (APPsw)", *Journal of Neurochemistry*, 2002, pp. 655-658, vol. 81.

Oddo, S. et al., "Chronic nicotine administration exacerbates tau pathology in a transgenic model of Alzheimer's disease", *Proceedings of the National Academy of Sciences of USA*, 2005, pp. 3046-3051, vol. 102.

Ono, K. et al., "Nicotine breaks down preformed Alzheimer's beta-amyloid fibrils in vitro", *Biological Psychiatry*, 2002, pp. 880-886, vol. 52.

Salomon, AR. et al., "Nicotine inhibits amyloid formation by the beta-peptide", *Biochemistry*, 1996, pp. 13568-13578, vol. 35.

Schuettelkopf, AW. et al., "PRODRG—a tool for high-throughput crystallography of protein-ligand complexes", *Acta Crystallographica*, 2004, pp. 1355-1363, vol. 60.

Szymanska, I. et al., "Electrochemical impedance spectroscopy for study of amyloid beta-peptide interactions with (−) nicotine ditartrate and (−) cotinine", *Biosens Bioelectron*, 2007, pp. 1955-1960, vol. 22.

Terry, AV, Jr. et al., "Cotinine, a neuroactive metabolite of nicotine: potential for treating disorders of impaired cognition", *CNS Drug Review*, 2005, pp. 229-252, vol. 11.

Tong, L. et al., "Beta-amyloid peptide at sublethal concentrations downregulates brain-derived neurotrophic factor functions in cultured cortical neurons", *Journal of Neuroscience* 2004, pp. 6799-6809, vol. 24.

Triguero, L. et al., "Comparative molecular dynamics studies of wild-type and oxidized forms of full-length Alzheimer amyloid beta-peptides Abeta(1-40) and Abeta(1-42)", *Journal of Physical Chemistry B*, 2008, pp. 7123-7131, vol. 112.

Unger, C. et al., "Early changes in Abeta levels in the brain of APPswe transgenic mice—implication on synaptic density, alpha7 neuronal nicotinic acetylcholine- and N-methyl-D-aspartate receptor levels", *Molecular & Cellular Neurosciences*, 2005, pp. 218-227, vol. 30.

Yolton, K., et al., "Exposure to environmental tobacco smoke and cognitive abilities among U.S. children and adolescents", *Environmental Health Perspectives*, 2005, pp. 98-103, vol. 113.

York, DM. et al., "Atomic-level accuracy in simulations of large protein crystals", *Proceedings of the National Academy of Sciences of USA*, 1994, pp. 8715-8718, vol. 91.

Bandyopadhyaya, G. et al. "Protective role of curcumin against nicotine-induced genotoxicity on rat liver under restricted dietary protein" *European Journal of Pharmacology*, Jul. 7, 2008, pp. 151-157, vol. 588(2-3).

Evans, M.S. et al. "Electrophysiology of embryonic, adult and aged rat hippocampal neurons in serum-free culture" *Journal of Neuroscience Methods*, Jan. 31, 1998, pp. 37-46, vol. 79(1).

Froeliger, B. et al. "Effects of nicotine on novelty detection and memory recognition performance: double-blind, placebo-controlled studies of smokers and nonsmokers" *Psychopharmacology*, Sep. 2009, pp. 625-633, vol. 205.

Peng, S. et al. "Decreased Brain-Derived Neurotrophic Factor Depends on Amyloid Aggregation State in Transgenic Mouse Models of Alzheimer's Disease" *Journal of Neuroscience*, Jul. 22, 2009, pp. 9321-9329, vol. 29(29).

Schnurr, P. et al. "Research on Posttraumatic Stress Disorder: Epidemiology, Pathophysiology, and Assessment" *Journal of Clinical Psychology*, 2002, pp. 877-889, vol. 58(8).

Wittchen, H. et al. "Posttraumatic Stress Disorder: Diagnostic and Epidemiological Perspectives" *CNS Spectr.*, Jan. 2009, pp. 5-12, vol. 14:(1 Suppl 1).

Eskandarian, S. et al. "Effects of systemic administration of oxytocin on contextual fear extinction in a rat model of post-traumatic stress disorder" *Basic Clin Neurosci*, 2013, 4(4):315-322.

Hawkins, K.A. and Cougle, J.R. "The effects of nicotine on intrusive memories in nonsmokers" *Exp Clin Psychopharmacol*, 2013, 21(6):434-442.

Knox, D. et al. "Single prolonged stress disrupts retention of extinguished fear in rats" *Learn Mem*, 2012, 19(2):43-49.

Kutlu, M.G. and Gould, T.J. "Acute nicotine delays extinction of contextual fear in mice" *Behav Brain Res*, 2014, 263:133-137.

Kutlu, M.G. et al. "The effects of acute nicotine on contextual safety discrimination" *J Psychopharmacol*, 2014, 28(11):1064-1070.

Lapiz-Bluhm, M.D. and Peterson, A.L. "Neurobehavioral mechanisms of traumatic stress in post-traumatic stress disorder" *Curr Top Behav Neurosci*, 2014, 18:161-190.

"Trauma- and Stressor-Related Disorders" in the Diagnostic and Statistical Manual of Mental Disorders, Fifth Edition, American Psychiatric Association, 2013, 22 pages.

* cited by examiner

FIG. 7B
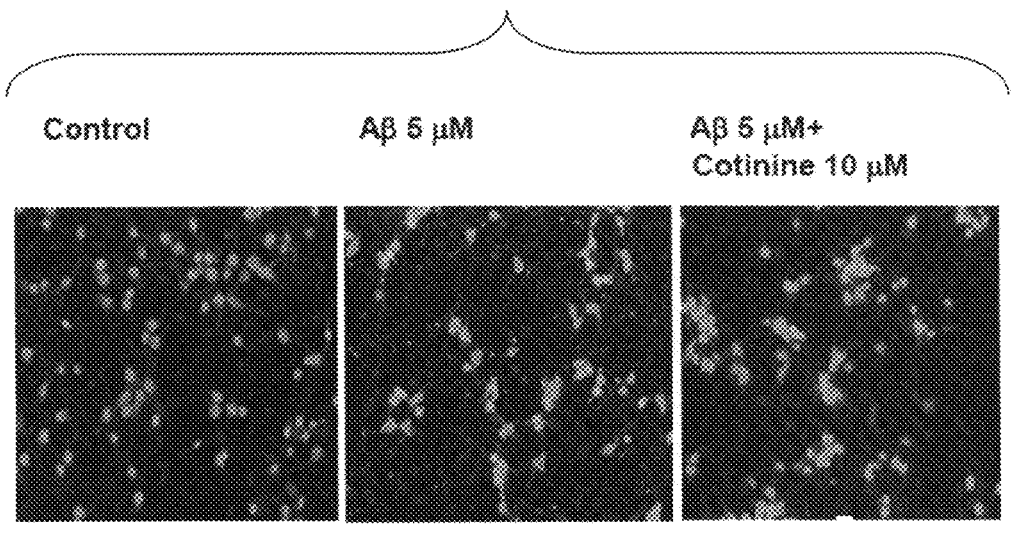
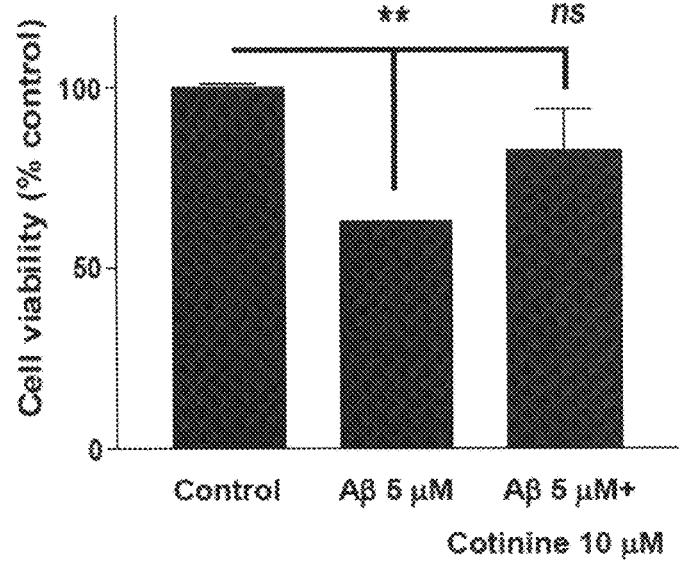
FIG. 7C

+H3N-DAEFRHDSGY EVHHQKLVFF AEDVGSNKGA IIGLMVGGVV IA-COO-

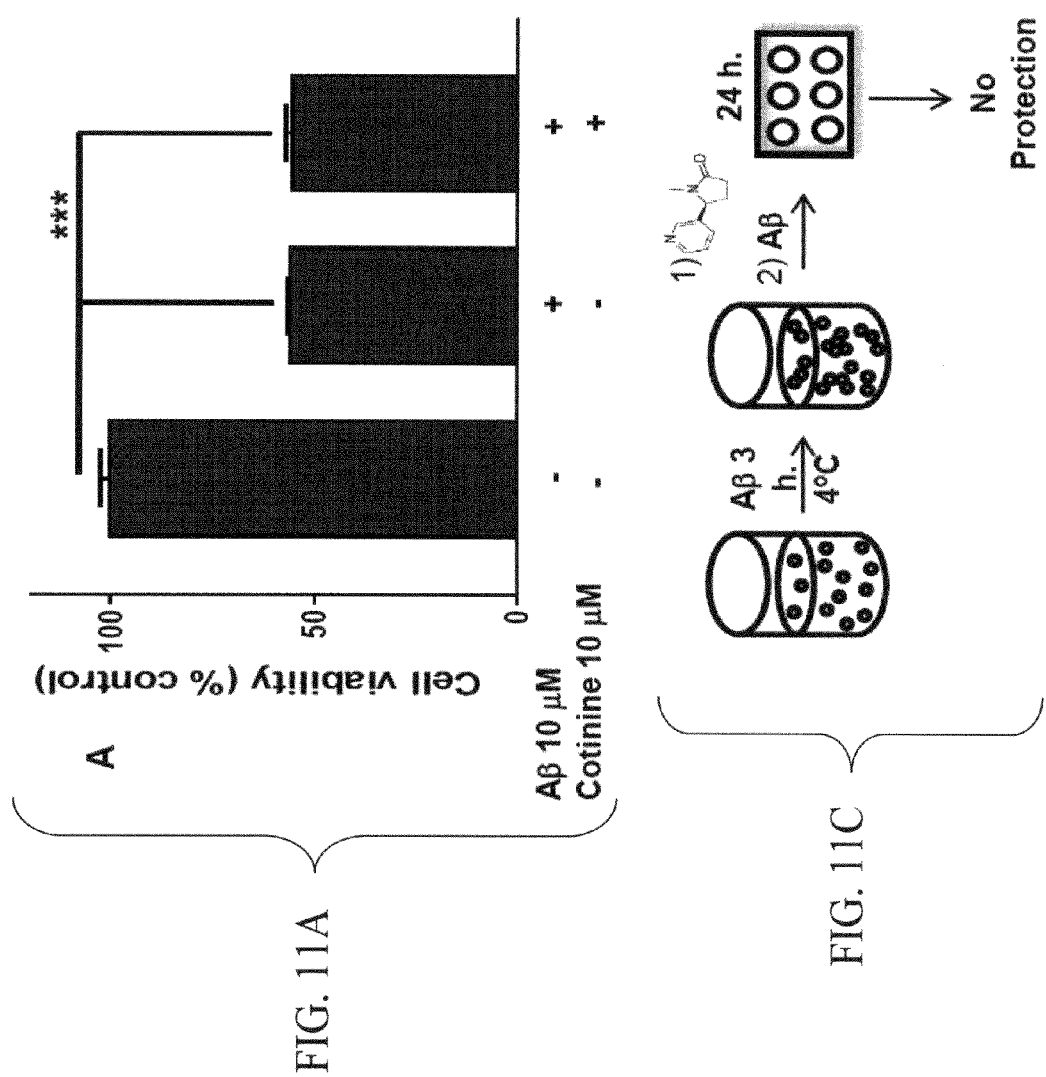

FIG. 14A                    FIG. 14B

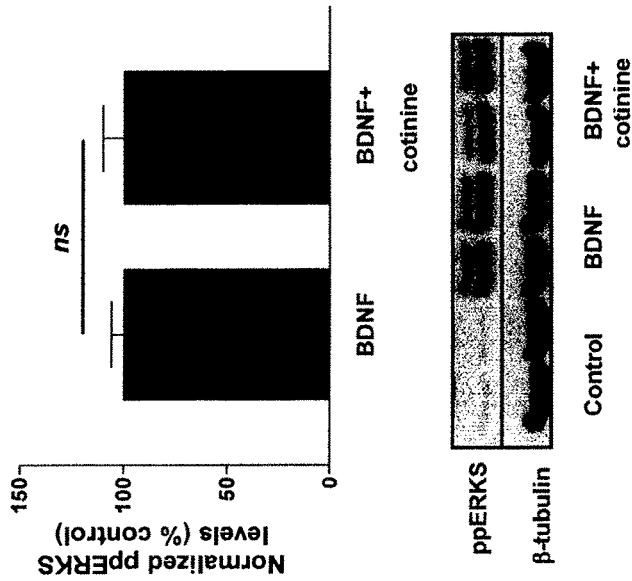
FIG. 17B
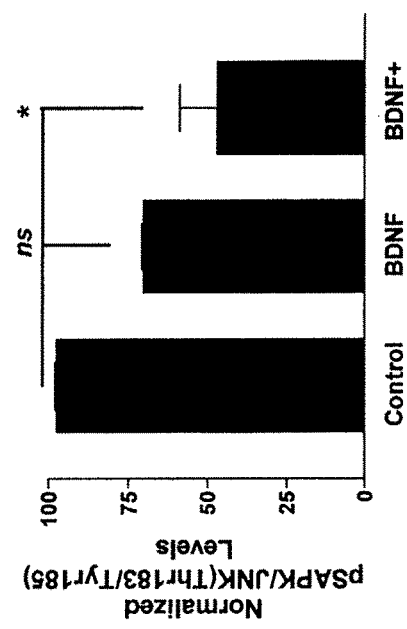
FIG. 17A
FIG. 17C
FIG. 17D

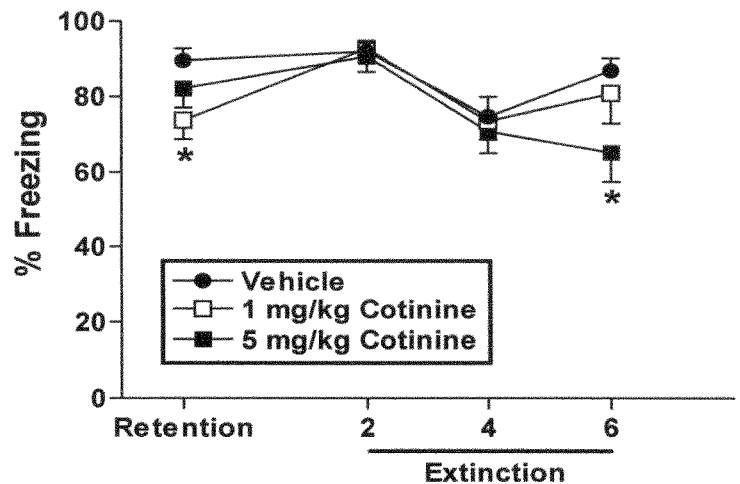
FIG. 18
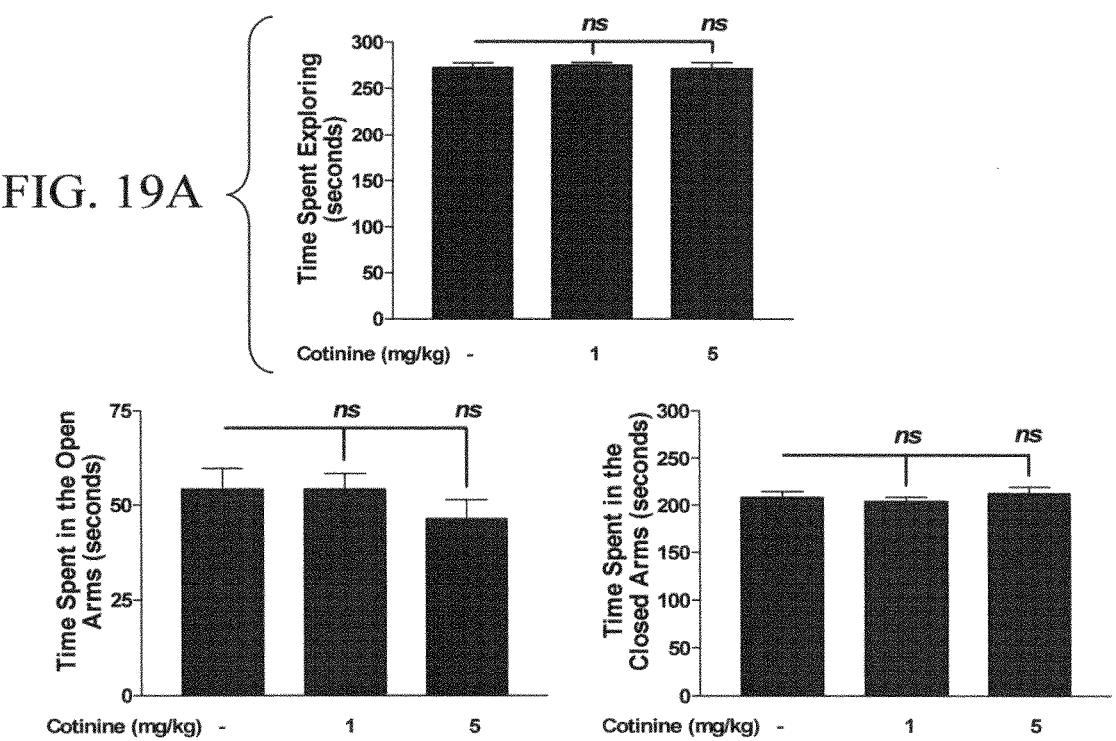
FIG. 19A
FIG. 19B
FIG. 19C

MATERIALS AND METHODS FOR DIAGNOSIS, PREVENTION AND/OR TREATMENT OF STRESS DISORDERS AND CONDITIONS ASSOCIATED WITH ABETA PEPTIDE AGGREGATION

CROSS-REFERENCE TO RELATED APPLICATIONS

The present application claims the benefit of U.S. Provisional Application Ser. No. 61/194,064, filed Sep. 24, 2008, and U.S. Provisional Application Ser. No. 61/099,746, filed Sep. 24, 2008, each of which is hereby incorporated by reference herein in its entirety, including any figures, tables, nucleic acid sequences, amino acid sequences, and drawings.

BACKGROUND OF THE INVENTION

Post-traumatic stress disorder (PTSD) is a type of anxiety disorder that manifests after exposure to a life-threatening traumatic event (Kessler (2000); Kessler et al. (1995)). PTSD affects approximately 6.8% of the American population and is caused by rape, assault, accidents or combat (Kessler et al. (2005)). In 2004, a US army study of more than 3600 veterans returning from Afghanistan and Iraq found that the percentage of veterans suffering from PTSD and related disorders, was 9.3% for those who served in Afghanistan and 17.1% for those who were stationed in Iraq (Hoge et al. (2004)). Compared with normal individuals, PTSD patients have a reported higher utilization of medical services (Calhoun et al. (2002); Solomon and Davidson (1997)), and are at increased risk for developing cardiovascular disease and cancer (Boscarino (2006); Schnurr and Jankowski (1999)).

Tobacco consumption is directly associated with PTSD. Numerous reports dealing with smoking among individuals with PTSD, mostly as a result of combat related trauma, showed that smoking prevalence is higher than in the normal population with rates ranging from 34% to 86%.

Alzheimer's disease (AD) is the main cause of dementia in the elderly and a progressive degenerative disease of the brain associated with advanced age. AD is characterized by the presence of extracellular amyloid senile plaques in the brain mainly consisting of amyloid-beta (Abeta or $A\beta$) peptide (that is generated by proteolytic processing of the trans-membrane protein amyloid precursor protein (APP)) and neurofibrillary tangles composed of aggregated tau protein (a microtubule associated protein). AD pathology is characterized at the neuronal level, by synaptic loss and cell death of selected neuronal populations (Echeverria and Cuello (2002)). There are approximately 17 million people affected by the disease world wide, and it is estimated that by 2050 there will be approximately 25 million affected in the United States. There are no effective therapeutic agents for this disease, new drugs and potential cures are being intensely investigated. According to many studies the aggregated form of $A\beta$ and not the monomeric form of the peptide is toxic. One of the strategies being investigated as a potential cure for AD is the search for molecules that are able to stop $A\beta$ aggregation. Thus, it is important to be able to detect $A\beta$ peptide in animal tissue.

Currently, a diagnosis of Alzheimer's disease is generally made using a psychiatric evaluation in conjunction with magnetic resonance imaging of central nervous system (CNS) for changes in morphology. Definitive diagnosis of Alzheimer's disease can only be made by post-mortem neuropathological examination of a patient's brain. Thus, it would be beneficial to have a means for diagnosing and monitoring Alzheimer's disease in a patient in vivo.

Down's syndrome (DS), also named as chromosome 21 trisomy, is a genetic disorder caused by the presence of an extra 21st chromosome. DS is characterized by impairment of cognitive abilities and physical changes and other health problems such as a higher risk for congenital heart defects, recurrent ear infections, obstructive sleep apnea, and thyroid dysfunctions. The incidence of DS is estimated at 1 per 800 to 1,000 births. The adult patients with DS have much higher incidence of Alzheimer's disease than non affected individuals. It has reported that 25% of persons with DS develop the disease by age 40, and the rate increases dramatically to 65% after age 60. Post-Mortem, nearly all adults that suffered from DS showed Alzheimer's disease pathology.

Tobacco smoke is composed of thousands of compounds, most of which have deleterious actions on cell homeostasis resulting in toxic effects over the cardiovascular, pulmonary and brain systems (Gallinat et al. (2006); Yolton et al. (2005)). Despite all of these negative actions, several studies suggest that smoking is protective against AD (Court et al. (2005); Merchant et al. (1999); Birtwistle and Hall (1996)) and Parkinson's disease (Hong et al. (2009)). The benefits of tobacco have been attributed to nicotine, an alkaloid and a potent cholinergic agonist present in tobacco (Doolittle et al. (1995); Levin (2002)). Nicotine has anti-apoptotic actions by a mechanism dependent on nicotinic acetylcholine receptors (nAChRs), and has neuroprotective activity against $A\beta$ toxicity in vitro (Gahring et al. (2003)). Using the transgenic mouse model of AD, Tg2576 (APPswe) (Hsiao et al. (1996)), it has been shown that nicotine reduces the levels of $A\beta$ in the brain and improves memory abilities in these mice (Nordberg et al. (2002); Unger et al. (2005); Hellstrom-Lindahl et al. (2004)). However, the short half-life, toxicity and potential negative effects in promoting tau pathology of nicotine discouraged its use in therapeutics (Oddo et al. (2005)).

Nicotine is metabolized to cotinine in the liver (Hammond et al. (1991)), which has a longer half-life than nicotine (10-24 h vs. 2-3 h, respectively) and similar cytoprotective activity (Terry et al. (2005)). The molecular mechanisms underlying the protective actions of cotinine are not well understood. Cotinine is a weak agonist at the nicotinic and muscarinic ACh receptors (mAChR), and it does not have significant cholinergic effects in the brain (Terry et al. (2005); Buccafusco et al. (2007); Briggs et al. (1995)).

In search of a mechanism of tobacco protection against AD, the effect of nicotine and cotinine on the aggregation of amyloidogenic fragments of $A\beta$ peptides has been explored in previous studies (Salomon et al. (1996); Szymanska et al. (2007); Kirschner et al. (2008)). The first study reported by Salomon et al. (1996) showed by using circular dichroism (CD) and ultraviolet spectroscopic techniques that nicotine and also but at a less extent cotinine inhibited amyloid formation by $A\beta_{1-42}$ peptide. Also by using nuclear magnetic resonance (NMR) analysis of the $A\beta$-nicotine complex, they suggested that the biologically active optical enantiomer of nicotine (L-(−)-nicotine, S form) inhibited the conversion of the $A\beta_{1-42}$ peptide from its soluble form into insoluble β-sheet oligomers. The effect was attributed to the interaction of the $A\beta_{1-42}$ residues His6, His13 and His14 via aromatic π-π and/or electrostatic interactions with the pyrrolidine moieties of nicotine (Salomon et al. (1996)).

In a recent study, x-ray fiber diffraction was used to screen $A\beta$ aggregation inhibitors (Kirschner et al. (2008)). These studies showed that $A\beta_{17-28}$ fibril formation was not inhibited by nicotine or cotinine whereas $A\beta_{12-28}$ was, from this evidence, the authors proposed that the binding of aromatic small molecules to the histidines present in the Aβ sequence 12-16 (VHHQK) may inhibit the subsequent Aβ oligomerization and interfibril aggregation (Kirschner et al. (2008)).

BRIEF SUMMARY OF THE INVENTION

The subject invention concerns materials and methods for treating and/or preventing diseases associated with the accumulation and/or aggregation of Aβ peptide in neural tissue. In one embodiment, a method of the invention comprises administering a therapeutically effective amount of cotinine, or a pharmaceutically acceptable salt thereof, to a person or animal in need of treatment. The methods of the invention can be used to treat Alzheimer's disease (AD) and Parkinson's disease (PD). In one embodiment, the method is used to treat a person having Down's syndrome.

The subject invention also concerns materials and methods for treating and/or preventing stress disorders, such as post-traumatic stress disorder (PTSD). In one embodiment, a method of the invention comprises administering a therapeutically effective amount of cotinine, or a pharmaceutically acceptable salt thereof, to a person in need of treatment.

The subject invention also concerns compositions that comprise cotinine, or a pharmaceutically acceptable salt thereof, and a pharmaceutically acceptable carrier, diluent or adjuvant.

The subject invention also concerns materials and methods for detecting, diagnosing, and monitoring conditions associated with accumulation of Aβ peptide in neural tissue, such as Alzheimer's disease and Parkinson's disease. In one embodiment, a method of the invention comprises administering detectably labeled cotinine to a person or animal. The level or concentration and/or location of labeled cotinine in neural tissue is then determined. The level of cotinine can be analyzed and a diagnosis made. In one embodiment, the cotinine is labeled with a radioisotope that can be detected by Position Emission Tomography (PET). Detection of labeled cotinine via PET provides for in vivo diagnosis and monitoring of a patient's condition. In one embodiment, Dementia associated with Parkinson's disease can be predicted by detection of labeled cotinine in striatum.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 7A-7C. Cotinine protects neurons against Aβ toxicity. Embryonic cortical neurons after 7 days in vitro (DIV) were treated with 5 μM Aβ either alone or with various concentrations of cotinine (0.1, 1, 10 μM). After 24 h cell viability was assessed using MTT assay (FIG. 7A) and double calcein-AM and PI staining (FIG. 7B). The MTT and calcein/PI staining values were normalized against control values considered 100%. The results show that even in the absence of pre-incubation with the peptide, cotinine decreased Aβ toxicity when added to the cell culture media. Scale bar=20 μm. The values represent the mean±S.E.M., with significant difference with P<0.05 (*), P<0.01 (), P<0.001 (*), between vehicle mean and treated samples mean.

FIG. 8C: Chemical structure of cotinine (upper), and $A\beta_{1-42}$ peptide sequence used in our studies (lower).

FIGS. 11A-11D. Cotinine is neuroprotective by blocking Aβ aggregation/oligomerization. The results show the viability of 7 DIV cortical cells exposed to pre-aggregated and fresh dissolved $A\beta_{1-42}$-cotinine solutions for 24 h at 37° C. FIG. 11A) MTT analysis of cell viability of cells treated with $A\beta_{1-42}$ solutions that were pre-incubated for 3 h at 4° C., and then added to the cell culture media containing 10 μM cotinine. FIG. 11B) MTT analysis of the cell viability of cortical cells treated with $A\beta_{1-42}$ pre-incubated with ascending concentrations of cotinine for 3 h at 4° C. The results indicate that when cotinine is added after a pre-aggregation step of the peptide it does not protect against Aβ toxicity, but when cotinine is pre-incubated with the $A\beta_{1-42}$ solution it is able to protect against toxicity. Plots represent cell viability as percentage of vehicle-treated controls. The results were considered significant with P<0.05 (*), and highly significant P<0.001 (***) as evaluated using One-way ANOVA with Tukey post test.

FIG. 12B: After treatment, cell extracts were analyzed by Western blot for the levels of the BDNF-stimulated phosphorylation of CREB (lower panel). The histogram (upper panel) represents the normalized levels of expression of phospho-CREB (Serine 133). β-tubulin was used as a control of protein loading and transfer. The values represent significant difference with P<0.5(*).

FIGS. 14A-14D. (FIG. 14A) The most representative structure derived from the 50 ns MD simulation on $A\beta_{1-42}$-cotinine complex. (FIG. 14B) Specific interactions of cotinine at the $A\beta_{1-42}$ binding site. (FIG. 14C) ChemDraw representation of specific interactions of cotinine at the $A\beta_{1-42}$ binding site. (FIG. 14D) Distance between the center of Tyr10 and pyridine nucleus of cotinine. The numbers represents the distances in Å.

(FIG. 15A) for the free $A\beta_{1-42}$ monomer. (FIG. 15B) For the $A\beta_{1-42}$-cotinine complex

FIGS. 17A-17D shows that cotinine selectively affects cell signaling in primary cortical neurons. After 7 days in vitro, cortical neurons were treated with BDNF (100 ng/ml) alone or BDNF plus cotinine (10 μM) for 1 h. After treatments, cells were lysed and whole cell extracts were analyzed for the active forms of JNK and ERKs, pJNK and pERK1/2 by Western blot.

FIG. 18 shows that cotinine enhanced the extinction of fear memory. Mice (n=8, by condition) were treated with vehicle or cotinine (1 and 5 mg/kg/day) for 8 days and then subjected to Fear conditioning training as described. After 24 hours (h) mice were tested for freezing behavior when re-exposed to the same context (the chamber) every day for 6 consecutive days.

FIGS. 19A-19C shows the effect of cotinine on basal anxiety levels in mice in the elevated plus maze test. Mice were placed in an EPM (Stoelting, Wood Dale, Ill., USA) made of grey plexiglas, consisting of two opposite-facing open arms, two opposite-facing closed arms, and a central area. Mice were placed at the end of one of the open arms facing toward the central area before a 5-minute test session was begun. We recorded the number of entries into the open and closed arms and assessed the exploratory behavior of the mice. We utilized a video tracking software that measures movement in each section of the maze in order to determine the time the mice were mobile exploring the different arms. Statistical significance was evaluated using One-way ANOVA with Tukey posttest. ns, not significant.

DETAILED DESCRIPTION OF THE INVENTION

Figure 1:
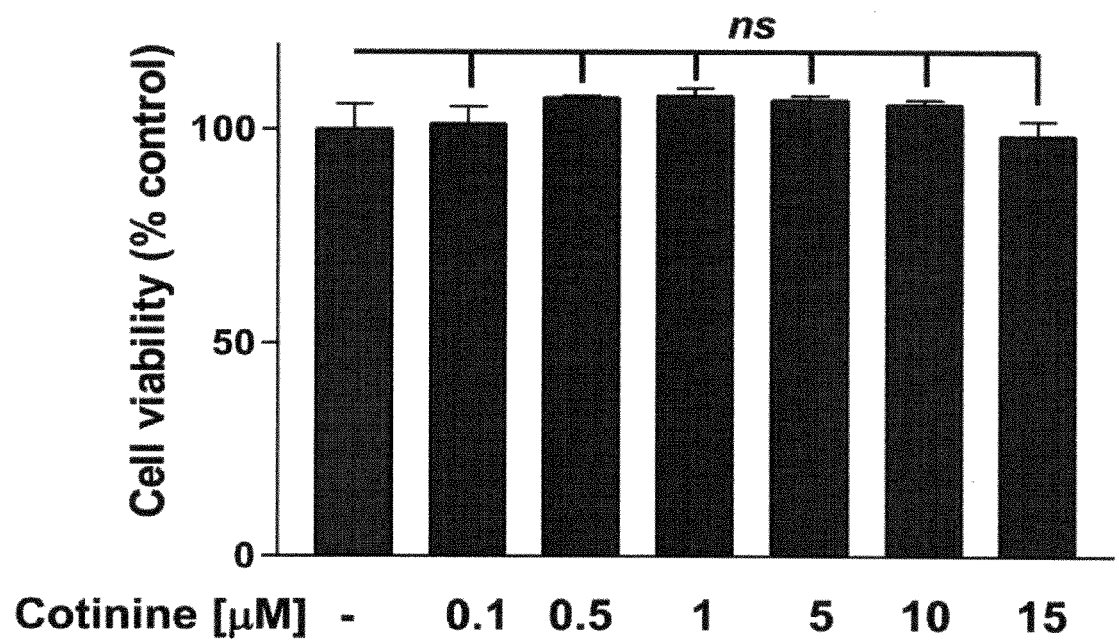
FIG. 1 shows survival of cortical cells exposed to cotinine as assayed in an MTT assay.

The subject invention concerns materials and methods for treating and/or preventing diseases associated with accumulation and/or aggregation of Abeta peptide in neural tissue. The methods of the invention can be used to treat and/or prevent neurodegenerative conditions, such as Alzheimer's disease (AD) and Parkinson's disease (PD). In one embodiment, a method of the invention comprises administering a therapeutically effective amount of cotinine, or a pharmaceutically acceptable salt thereof, to a person or animal in need of treatment. In one embodiment, cotinine can be administered in conjunction with other drugs for the treatment or prevention of neurodegenerative conditions, including, for example, donepezil (ARICEPT), galantamine (RAZADYNE), rivastigmine (EXELON), memantine (AKATINOL), rasagiline (AZILECT), selegiline (EL-DEPRYL), L-dopa (LEVODOPA, SINEMET, PARCOPA, STALEVO, MADOPAR), carbidopa (LODOSYN), and benserazide, or an isomer or analog thereof. Other neurodegenerative conditions contemplated within the scope of the present invention include, but are not limited to, dementia with Lewy bodies (DLB), dementia pugilistica, Pick's disease, cerebral amyloid angiopathy, and posterior cortical atrophy.

The methods of the invention can also be used to treat and/or prevent disorders associated with Down's syndrome. In one embodiment, a therapeutically effective amount of cotinine, or a pharmaceutically acceptable salt thereof, is administered to a person having Down's syndrome.

The subject invention also concerns methods for treating and/or preventing stress disorders, such as PTSD. In one embodiment, a method of the invention comprises administering a therapeutically effective amount of cotinine, or a pharmaceutically acceptable salt thereof, to a person or animal in need of treatment. In one embodiment, cotinine can be administered in conjunction with other drugs for the treatment of stress disorders, including, for example, monoamine oxidase (MAO) inhibitors; antiepileptic drugs; selective serotonin reuptake inhibitors (SSRI), such as citalopram, escitalopram, fluvoxamine, paroxetine, and sertraline; serotonin-norepinephrine reuptake inhibitors (SNRI), such as venlafaxine, desvenlafaxine, duloxetine, sibutramine, and milnacipran; tricyclic antidepressants (TCAs); 3,4-methylenedioxy-N-methylamphetamine (MDMA); propranolol; clonidine, and ziprasidone, or an isomer or analog thereof. Methods of the invention can be used in combination with other therapies for stress disorders, including, for example, various forms of psychotherapy, yoga, and the like.

The subject invention also concerns compositions that comprise cotinine, or a pharmaceutically acceptable salt thereof, and a pharmaceutically acceptable carrier, diluent or adjuvant. In one embodiment, a composition of the invention further comprises one or more drugs or compounds useful in treating AD, PD, or PTSD. Cotinine has the chemical structure:

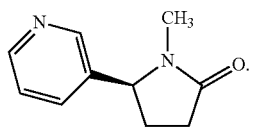

Isomers and racemates of cotinine are contemplated within the scope of the methods and compositions of the present invention. In one embodiment, cotinine is racemic cotinine. In another embodiment, cotinine is the (−)-isomer (i.e., (−)-cotinine). In a further embodiment, cotinine is the (+)-isomer (i.e., (+)-cotinine).

The subject invention also concerns methods for inhibiting or preventing cell death resulting from Aβ oligomerization. In one embodiment, the method comprises contacting a cell with an effective amount of cotinine, or a physiologically acceptable salt thereof. In one embodiment, the cell is a neural cell. In a specific embodiment, the cell is a cortical cell. In one embodiment, the cell is contacted with cotinine in vivo or in vitro.

The subject invention also concerns methods for inhibiting or preventing Aβ oligomerization in a cell. In one embodiment, the method comprises contacting a cell with an effective amount of cotinine, or a physiologically acceptable salt thereof. In one embodiment, the cell is a neural cell. In a specific embodiment, the cell is a cortical cell. In one embodiment, the cell is contacted with cotinine in vivo or in vitro.

The subject invention also concerns materials and methods for increasing activity or expression of dopamine- and cyclic AMP-regulated phosphoprotein of 32 kDa (DARPP-32) and/or facilitating serotonin release in the brain. In one embodiment, the method comprises contacting a cell with an effective amount of cotinine, or a physiologically acceptable salt thereof. In one embodiment, the cell is a neuron. In a specific embodiment, the cell is a cortical cell.

The subject invention concerns materials and methods for detecting, diagnosing, and/or monitoring conditions associated with accumulation and/or aggregation of Aβ peptide in neural tissue, such as Alzheimer's disease and Parkinson's disease. In one embodiment, a method of the invention comprises administering detectably labeled cotinine to a person or animal. The method of the invention optionally comprises labeling cotinine with a detectable label. The cotinine can be administered through any suitable route, e.g., intravenously. The labeled cotinine is then detected, e.g., via radioimaging. The level or concentration and/or location of labeled cotinine in neural tissue can be determined and/or analyzed and a diagnosis made. In one embodiment, the cotinine is labeled with a radioisotope that can be detected by Positron Emission Tomography (PET). PET detectable radioisotopes include, for example, carbon-11, nitrogen-13, oxygen-15, fluorine-18, bromine-76, and iodine-121. In another embodiment, cotinine is labeled with a radioisotope that can be detected using single photon emission computed tomography (SPECT). SPECT detectable radioisotopes include, for example, 99m-Technetium, 123-iodine, and 111-indium. PET and SPECT techniques using compounds other than cotinine are known in the art and can be applied to the use of cotinine in practicing the present invention. Methods of the invention using labeled cotinine can also be practiced in conjunction with other imaging agents such as Pittsburgh Compound B (PIB) and "C-BF-227" (Kudo et al., 2007). Methods of the invention can also be used in conjunction with other imaging systems such as computed tomography (CT) and magnetic resonance imaging (MRI) for detecting and/or diagnosing conditions associated with Aβ peptide. In one embodiment, Parkinson's disease can be diagnosed by detection of cotinine in striatum.

Radiolabeled cotinine of the invention can be administered at any suitable dose as determined for a particular application by an ordinarily skilled clinician. In one embodiment, radiolabeled cotinine may be administered at a dose of about 1 to 100 mCi per 70 kg of body weight. The radiolabeled cotinine can be administered, for example, in a physiologically acceptable solution, such as a physiologically acceptable saline solution.

The subject invention also concerns methods for identifying and evaluating the efficacy of drugs for treatment of disease associated with Aβ accumulation and/or aggregation. The levels, location, and/or changes in Aβ peptide accumulation and/or aggregation in a tissue can be determined before, during, and after the treatment regimen. In one embodiment, the level, location and/or changes of Aβ accumulation in neural tissue (as indicated by the presence of labeled cotinine) in a subject is determined using a method of the invention. The subject is then treated with the drug or therapeutic of interest. The level and/or location of Abeta during and/or after treatment is monitored and analyzed using a method of the invention. The efficacy of the drug can be evaluated by monitoring and analyzing Abeta changes in the subject's neural tissue as a result of the treatment.

Specific Embodiments Include:

A. A method for identifying and evaluating the efficacy of a drug or therapeutic for treatment of a disease or condition associated with Aβ accumulation and/or aggregation in a neural tissue, wherein said method comprises i) administering detectably labeled cotinine, or an isomer or racemate thereof, to a person or animal to determine the level or concentration and/or location of Aβ accumulation and/or aggregation in said tissue; ii) treating the person or animal with said drug or therapeutic; iii) monitoring and/or analyzing changes in the level or concentration and/or location of Aβ accumulation and/or aggregation in said tissue following said drug or therapeutic treatment.

B. The method according to embodiment A, wherein said labeled cotinine is detected using radioimaging.

C. The method according to embodiment A, wherein the level or concentration and/or location in neural tissue of said labeled cotinine is determined and/or analyzed.

D. The method according to embodiment A, wherein said labeled cotinine is labeled with a radioisotope.

E. The method according to embodiment D, wherein said radioisotope is detectable by Position Emission Tomography (PET) and/or single photon emission computed tomography (SPECT).

F. The method according to embodiment E, wherein said radioisotope is carbon-11, nitrogen-13, oxygen-15, fluorine-18, bromine-76, iodine-121, technetium-99m, iodine-123, or indium-111.

G. The method according to embodiment A, wherein said method further comprises administering one or more imaging agents.

H. The method according to embodiment G, wherein said imaging agent is Pittsburgh Compound B (PIB) or "C-BF-227".

I. The method according to embodiment A, wherein the condition is Parkinson's disease or Alzheimer's disease.

J. The method according to embodiment A, wherein detection of said labeled cotinine in striatum is indicative of Parkinson's disease.

K. The method according to embodiment A, wherein said labeled cotinine is radiolabeled and administered at a dose of about 1 mCi per 70 kg of body weight to about 100 mCi per 70 kg of body weight.

L. The method according to embodiment A, wherein said labeled cotinine is administered in a physiologically acceptable carrier, buffer, or diluent.

The subject invention also concerns a detectably labeled cotinine molecule. In one embodiment, the cotinine is radiolabeled. In a specific embodiment, the cotinine is labeled with a radioisotope suitable for PET or SPECT detection. PET detectable radioisotopes include, for example, carbon-11, nitrogen-13, oxygen-15, fluorine-18, bromine-76, and iodine-121. SPECT detectable radioisotopes include, for example, 99m-Technetium, 123-iodine, and 111-indium. The labeled cotinine can be provided in a physiologically acceptable carrier, buffer, or diluent.

The subject invention also concerns kits comprising in one or more containers: cotinine or a composition comprising cotinine, or a pharmaceutically acceptable salt and/or analog thereof, and optionally one or more compounds used to treat or prevent neurodegenerative conditions or stress disorders. In one embodiment, a kit of the invention comprises one or more of donepezil, galantamine, vivastigmine, memantine, or selegiline. In another embodiment, a kit comprises one or more of monoamine oxidase (MAO) inhibitors; antiepileptic drugs; selective serotonin reuptake inhibitors (SSRI), such as citalopram, escitalopram, fluvoxamine, paroxetine, sertraline, rasagiline, selegiline, L-dopa, carbidopa, and benserazide, or an isomer or analog thereof; serotonin-norepinephrine reuptake inhibitors (SNRI), such as venlafaxine, desvenlafaxine, duloxetine, sibutramine, and milnacipran; tricyclic antidepressants (TCAs); 3,4-methylenedioxy-N-methylamphetamine (MDMA); propranolol; clonidine, and ziprasidone, or an isomer or analog thereof. Kits of the invention can optionally include pharmaceutically acceptable carriers and/or diluents. In one embodiment, a kit of the invention comprises cotinine labeled with a detectable label, or composition comprising the labeled cotinine. In one embodiment, the cotinine is labeled with a radioisotope that can be detected by Positron Emission Tomography (PET). PET detectable radioisotopes include, for example, carbon-11, nitrogen-13, oxygen-15, fluorine-18, bromine-76, and iodine-121. In another embodiment, cotinine is labeled with a radioisotope that can be detected using single photon emission computed tomography (SPECT). SPECT detectable radioisotopes include, for example, 99 m-Technetium, 123-iodine, and 111-indium. In one embodiment, a kit of the invention includes one or more other components, adjuncts, or adjuvants as described herein. In one embodiment, a kit of the invention includes instructions or packaging materials that describe how to administer and/or how to use a compound or composition of the kit for the treatment of a stress disorder, Down's syndrome, or a neurodegenerative condition, or for detection, diagnosis, and/or monitoring a condition associated with Aβ peptide accumulation and/or aggregation in a tissue. Containers of the kit can be of any suitable material, e.g., glass, plastic, metal, etc., and of any suitable size, shape, or configuration. In one embodiment, a compound of the invention is provided in the kit as a solid, such as a tablet, pill, chewing gum, or powder form. In another embodiment, a compound of the invention is provided in the kit as a liquid or solution. In one embodiment, the kit comprises an ampoule or syringe containing a compound of the invention in liquid or solution form.

Specific Embodiments Include:

A. A kit comprising in one or more containers:

i) a cotinine molecule, or a composition comprising said cotinine molecule; and optionally ii) one or more other drugs useful in treating a neurodegenerative disorder, Down's syndrome, or a stress disorder.

B. The kit according to embodiment A, wherein said kit comprises donepezil (ARICEPT), galantamine (RAZADYNE), rivastigmine (EXELON), memantine (AKATINOL), selegiline (ELDEPRYL), a selective serotonin reuptake inhibitor (SSRI), a serotonin-norepinephrine reuptake inhibitor (SNRI), a tricyclic antidepressant (TCA), 3,4-methylenedioxy-N-methylamphetamine (MDMA), propranolol, clonidine, or ziprasidone, or an isomer or analog thereof, or a pharmaceutically acceptable salt thereof.

C. The kit according to embodiment A, further comprising instructions and/or packaging materials that describe how to use and/or administer a cotinine molecule or composition of the kit for treating a neurodegenerative disorder, Down's syndrome, or a stress disorder.

D. The kit according to embodiment A, wherein the cotinine molecule is labeled with a detectable label.

E. The kit according to embodiment A, further comprising a pharmaceutically acceptable carrier and/or diluent.

To provide for the administration of dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The compounds of the present invention include all hydrates and salts that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

It will be appreciated by those skilled in the art that certain of the compounds of the invention may contain one or more asymmetrically substituted carbon atoms which can give rise to stereoisomers. It is understood that the invention extends to all such stereoisomers, including enantiomers, and diastereoisomers and mixtures, including racemic mixtures thereof.

In vivo application of the subject compounds, and compositions containing them, can be accomplished by any suitable method and technique presently or prospectively known to those skilled in the art. The subject compounds can be formulated in a physiologically- or pharmaceutically-acceptable form and administered by any suitable route known in the art including, for example, oral, nasal, rectal, and parenteral routes of administration. As used herein, the term parenteral includes subcutaneous, intradermal, intravenous, intramuscular, intraperitoneal, and intrasternal administration, such as by injection. Administration of the subject compounds of the invention can be a single administration, or at continuous or distinct intervals as can be readily determined by a person skilled in the art.

The compounds of the subject invention, and compositions comprising them, can also be administered utilizing liposome technology, slow release capsules, implantable pumps, and biodegradable containers. These delivery methods can, advantageously, provide a uniform dosage over an extended period of time. The compounds of the invention can also be administered in their salt derivative forms or crystalline forms.

Compounds of the subject invention can be formulated according to known methods for preparing physiologically acceptable compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds based on the weight of the total composition including carrier or diluent.

Compounds of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Compounds and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Mammalian species that benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo bison, horses, donkey, swine, sheep, and goats; exotic animals typically found in zoos such as bear, lions, tigers, panthers, elephants, hippopotamus, rhinoceros, giraffes antelopes, sloth, gazelles, zebras, wildebeests, prairie dogs, koala bears, kangaroo opossums, raccoons, pandas, hyena, seals, sea lions, elephant seals, otters, porpoises dolphins, and whales. As used herein, the terms "subject" "host", and "patient" are used interchangeably and intended to include such human and non-human mammalian species.

The effect of cotinine on Aβ toxicity in cultured cortical neurons has been determined. After 7 days in vitro cells were treated with 5 µM Aβ alone or in the presence of cotinine for 24 hours. After this time cell survival was assessed by MTT and PI/Calcein-AM assays. The results showed that cotinine protected neurons against Aβ toxicity and increased cell survival from 76% (Aβ alone) to 85% (Aβ+10 µM cotinine) of vehicle-treated control cells as assessed using MTT assay. Similar results were obtained using PI and calcein-AM dyes. To determine whether the neuroprotection by cotinine involved the activity of the nAChRs, the effect of cotinine on Aβ toxicity was studied on cortical cells pre-treated with 10 nM α-Bgt and mecamylamine.

The results showed that α-Bgt was able to reverse the beneficial actions of nicotine against Aβ toxicity but not those of cotinine. We then investigated whether cotinine affected Aβ oligomerization by pre-incubating Aβ plus cotinine together, and then performing the toxicity assay and investigating the presence of Aβ oligomers by dot blot. The results suggest that cotinine protects cortical cells against Aβ toxicity by inhibiting Aβ oligomerization and by a mechanism that does not involve cotinine as an agonist of the nAChRs.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Materials and Methods for Examples 1-7

Western Blot. Cell protein extracts were separated by SDS-PAGE4-20%, transferred to nitrocellulose membranes, blocked with 5% skim milk in PBS-Tween 0.05%, and incubated with polyclonal antibodies against pCREB, β-tubulin, and GADPH overnight and after washing incubated with appropriate secondary antibodies for 1-2 hours. Immunoreactive bands were visualized using ECL.

Aβ toxicity assay. Primary cortical embryonic rat neurons were incubated with 5 µM Aβ in the presence or absence of various concentrations cotinine for 4 hours as described (Echeverria et al. (2005)). Cell viability was assessed using the MTT assay (Sigma). As an alternative approach cell viability after exposure to Aβ and cotinine was assessed using the vital dye calcein-AM (green fluorescence) to stain live cells and propidium iodide to stain dead cells. MTT values were normalized to control values considered 100%.

Dot Blot. The dot blot analysis was performed as described (Necula et al. (2007)). 3 µl of the oligomerization mix were applied onto nitrocellulose membranes and left to dry. After drying, the membranes were blocked for 1 hour at room temperature with 10% skim milk in TBS containing 0.05% Tween20 (TBS-T). The membranes were washed and incubated with the Aβ 6E10 (1 mg/ml) diluted in TBS-T containing 5% milk overnight at room temperature. After washing with TBS-T membranes were incubated with horseradish peroxidase-conjugated secondary antibody (1:5000) for 1 hour and analyzed using ECL.

Example 1—The Survival of Cortical Neurons is not Affected by Cotinine

Cortical cells were subjected to various concentrations of cotinine and cell viability was assessed after 48 hours by MTT assay (see FIG. 1). Statistical significance of the differences in MTT values was assessed by one-way ANOVA with Tukey post-test. ns, not significant difference with (P>0.05).

Example 2—Cotinine Protects Neurons Against Aβ Toxicity

Figures 2A, 2B:
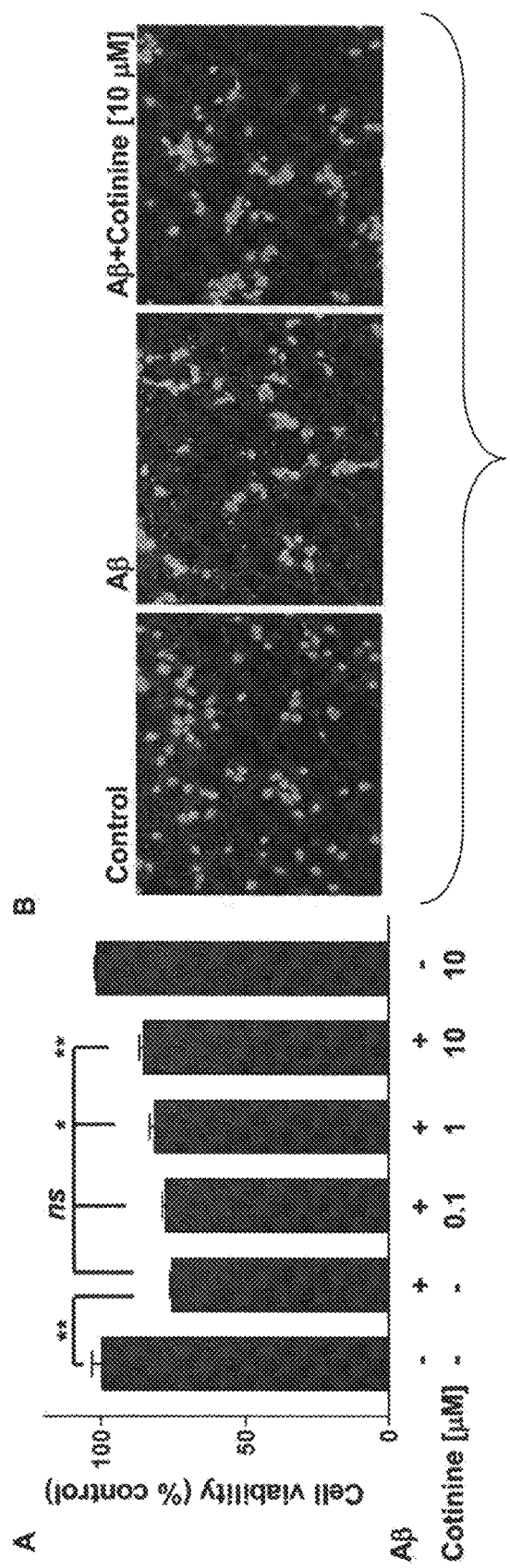
FIGS. 2A-2C and 2B show cortical cells protected by cotinine as assayed in an MTT assay.
Figure 2C:
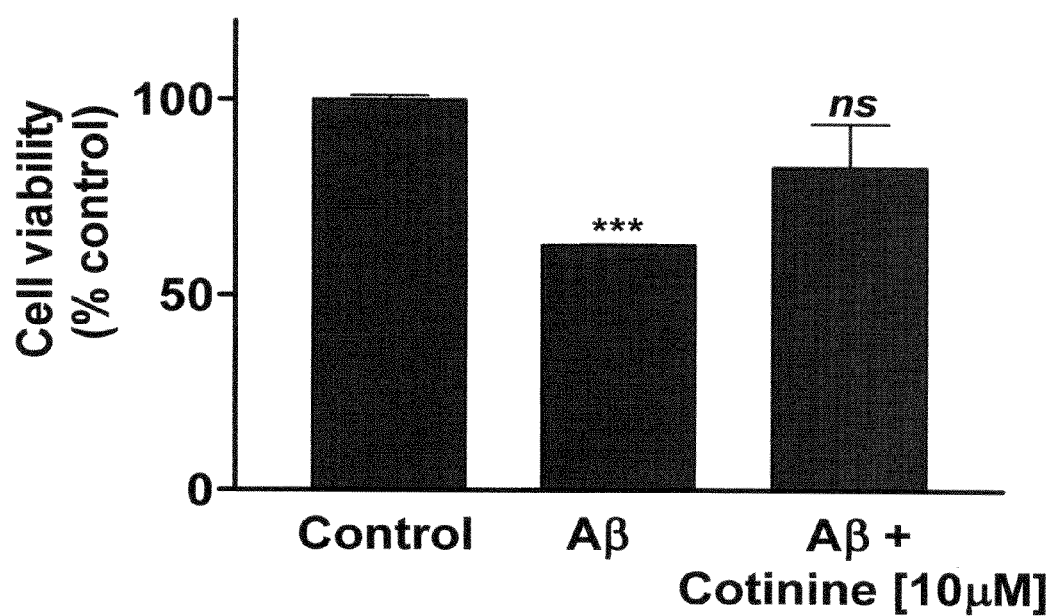

After 7 days in vitro, cortical neurons were treated with 5 µM Aβ, either alone or with various concentrations of cotinine (0.1, 1, 10 µM). After 24 hours cell viability was assessed using MTT assay (FIG. 2A) and double calcein-AM and PI staining (FIG. 2B). MTT values were normalized against control values considered 100%. The calcein-AM and PI staining was performed in the cortical cells subjected to Aβ toxicity for 24 hours. After 30 minutes, stained cells were analyzed by fluorescence microscopy. Scalebar=20 µm. The values represent the mean±S.E.M., with significant difference with P<0.05, *(P<0.05), (P<0.01), *(P<0.001), between vehicle mean and treated samples mean.

Example 3—Cotinine is Neuroprotective by Blocking Aβ Oligomerization

Figures 3A, 3B:
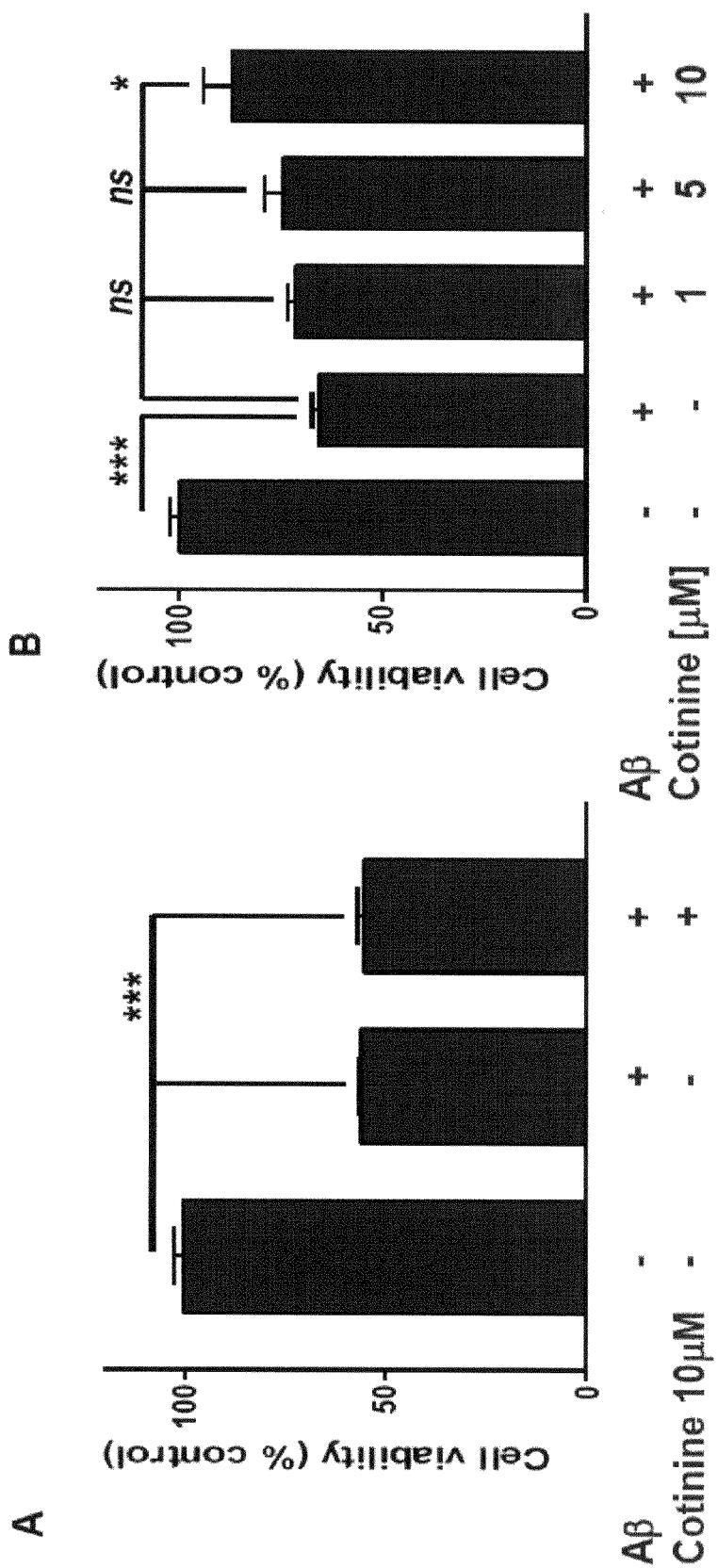
FIGS. 3A and 3B show cotinine inhibits Aβ oligomerization as assayed by MTT assay.

After 7 days in vitro, cortical cells were treated with an Aβ$_{1-42}$ solution pre-incubated for 3 hours at 4° C. before being added to the culture media containing 10 μM cotinine. After 24 hours of treatment cell viability was assessed using MTT assay. In FIG. 3A, different solutions of 5 μM Aβ peptide or Aβ plus cotinine, was added to the culture media after a pre-incubation step in PBS in the presence or absence of different concentrations of cotinine for 3 hours. After 24 hours of treatment, cortical cell viability was assessed using MTT assay. In FIG. 3B, the 20× Aβ solution was prepared by pre-incubating 200 μM Aβ solution in PBS for 3 hours at 4° C. in the presence or absence of ascending concentrations of cotinine (50, 100, 200, 500 μM), when the solutions were added they were diluted to the concentrations indicated. The histograms represent the cell viability as percentage of vehicle-treated controls. The results were considered not significant, ns with $P>0.05$, significant with $P<0.05(*)$, and highly significant $P<0.01(***)$ as evaluated using One-way ANOVA with turkey post test.

Figure 4A:
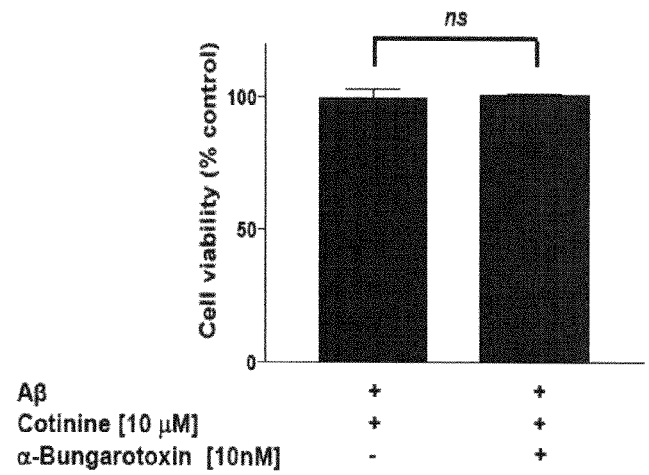
FIGS. 4A and 4B show neuroprotective activity of cotinine is not affected by the antagonist of the nAChR alpha-bungarotoxin and mecamylamine.
Figure 4B:
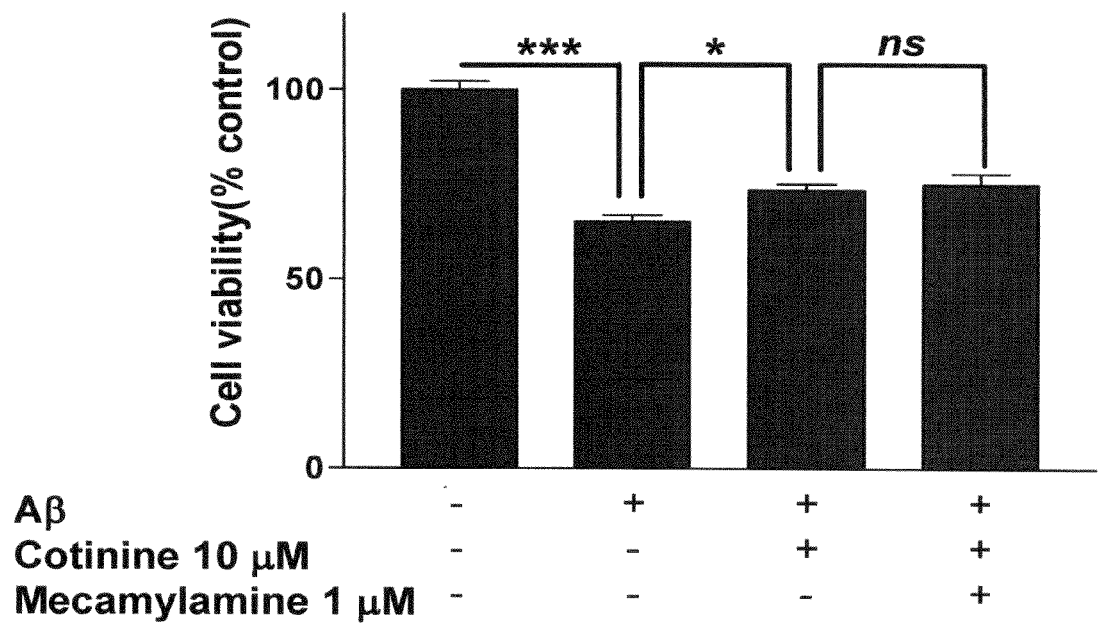

Example 4—Cotinine is not an Agonist of the nAChRs 7 days in vitro, cortical neurons were pretreated or not with the α-7 nAChR antagonist α-Bgt (10 nM) and then treated with Aβ (5 μM), alone and/or with various concentrations of cotinine (0.1, 1 and 10 μM). After 24 hours cell viability was assessed using MTT assay (FIG. 4A). Cortical neurons after 7 days in vitro were treated with the nonselective nAChR antagonist (1 μM) alone or in the presence of cotinine (10 mM). After 24 hours, cell viability was assessed using MTT assay (FIG. 4B). MTT values represent the mean±S.E.M., with significant difference with $P<0.05$, *($P<0.05$), *** ($P<0.001$), between vehicle mean and treated samples mean.

Example 5—Cotinine Inhibits Aβ Oligomerization

Figure 5:
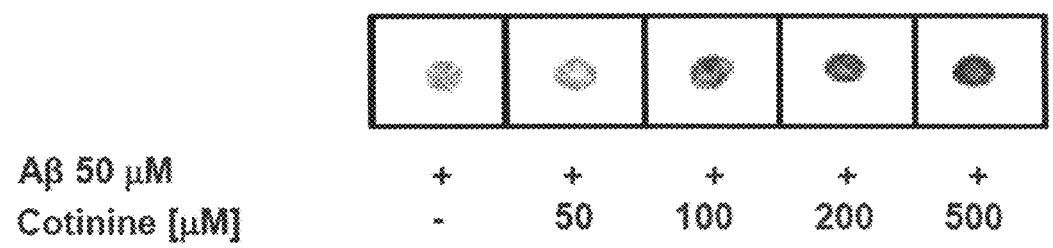
FIG. 5 shows a dot blot using antibody 6E10.

Aliquots of an Aβ oligomerization mix were analyzed using the Aβ antibody 6e10 by Dot Blot after 3 days of incubation at room temperature. Briefly, Aβ (50 μM) was subjected to oligomerization conditions in the presence or absence of cotinine (50, 100, 200, 500 μM) and aliquots were analyzed using the Aβ antibody 6E10 as described in "Materials and Methods". The results are shown in FIG. 5.

Figure 6A:
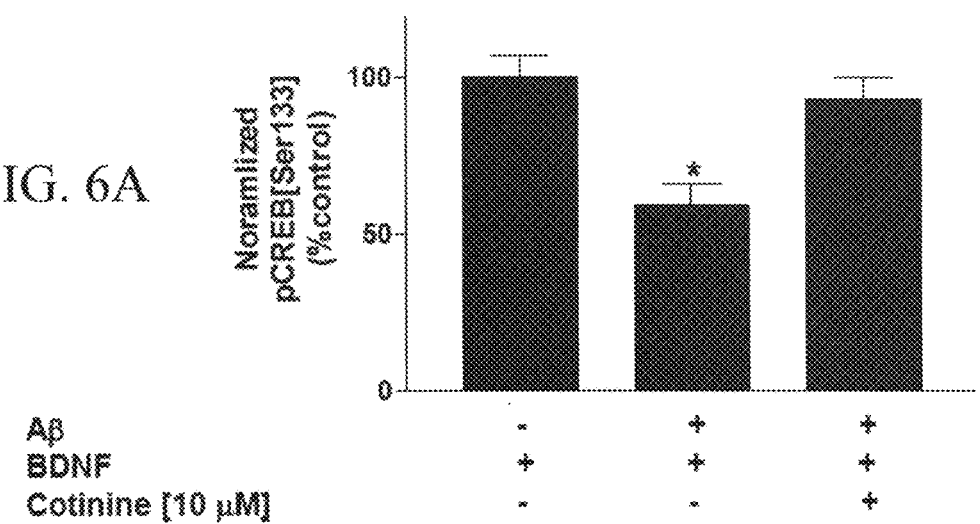
FIGS. 6A and 6B show a Western blot.
Figure 6B:
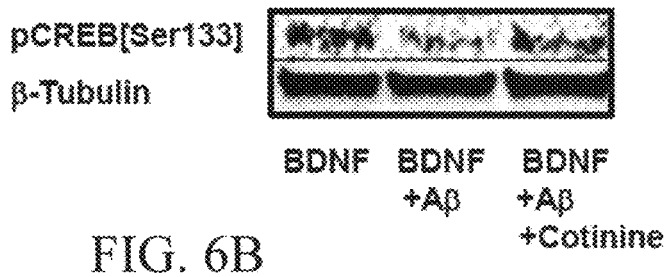

Example 6—Cotinine Restores the BDNF-Stimulated Phosphorylation of CREB in Cortical Cells Western blot analysis of the BDNF-stimulated phosphorylation of CREB in extracts of cortical cells. Cells were exposed to vehicle, 5 μM Aβ alone or 5 μM Aβ plus 10 μM cotinine for 5 hours, then to BDNF (50 ng/ml) for 1 hour and analyzed for CREB by western blot (FIG. 6B). The histogram (FIG. 6A) represents the levels of phospho-CREB (Ser133) normalized against β-Tubulin used as a control of protein loading. The values represent significant (*) difference with $P<0.05$.

Example 7

It has been discovered that cotinine protects brain cortical cells against the toxicity of the Amyloid beta peptide. The cortical cells were exposed to 5 microM Aβ for 24 hours and 48 hours and analyzed for cell viability using two viability tests. Cell viability was quantified by MTT and propidium iodide (PI) and calcein-AM staining assays. MTT assay measures the mitochondrial conversion of the tetrazolium salt MTT (3-(4,5-dimethylthiazol-2-yl)-2,5-diphenyl tetrazolium bromide) to formazan. To perform the MTT assay the cell culture medium was replaced with medium containing MTT (0.5 mg/mL). Following 1-4 h of incubation at 37° C., MTT formazan crystals were dissolved in DMSO and absorbance at 570 nm was measured. Absorbance values are a measure of cell viability. MTT results are expressed as percentage of vehicle treated controls. MTT assays were performed by measuring the levels of formazan after dissolving the precipitates in DMSO. The double calcein-AM and PI staining, involves staining with PI (a fluorescent nucleic acid dye used for the staining of dead cells) and calcein-AM a compound that inside of live brain cells, is converted to the green fluorescent compound calcein. After 30 minutes of incubation of the cells with these compounds were washed and analyzed by fluorescence microscopy. The results show that cotinine protects neurons against the toxicity of Aβ peptide, a peptide that accumulates in the brain of AD patients, and is neurotoxic. Cotinine inhibits Abeta oligomerization and prevents its toxicity on cortical neurons.

The neuroprotective actions of cotinine are independent of the nicotininc Acetylcholine receptors (nAChR) as it was not affected by alpha-Bungarotoxin, or mecamylamine nAChRs antagonists.

Cotinine can also be beneficial against post-traumatic stress disorders, as we discovered that cotinine increases the activity of DARPP-32 in neurons from rat brain cells. DARPP-32 stimulates cAMP signaling a molecular mechanism that favors the brain plasticity that is required to "forget" traumatic memories that increase anxiety and psychological suffering in post-traumatic stress disorders. Cotinine also facilitates serotonin release and prevent psychosis related behavioral abnormalities in rats. Thus, cotinine can be useful in treating PTSD patients and can act as a serotonin reuptake inhibitor in addition to its neuroprotective actions.

Materials and Methods for Examples 8-13

Drugs. Cotinine was purchased from Sigma Chemical Company (Saint Louis, Mo., USA).

Cortical cells. Embryonic rat cortical neurons were cultured following the protocol described (Brewer (1995)) but using embryonic cortical tissues obtained from Brain Bits LLC (Springfield, Ill., USA). The brain tissues were dissociated by 0.05% (v/v) trypsin digestion and dissociated by repeated passages through a pipette tip. Cortical cells ($2 \times 10^5$ cells, 1,250 cells/mm$^2$) were plated in Neurobasal E medium, supplemented with 2% B27, and 1 mM Glutamax and plated onto 20-mm tissue culture wells coated with poly-D-lysine (0.1 mg/ml). Then cortical cells were incubated at 37° C. in a humidified incubator with 95% air/5% $CO_2$ for 7-10 days, before being used for cell viability and protein expression analysis.

Preparation of Aβ oligomers. $A\beta_{1-42}$ peptide was obtained from American Peptide (Sunnyvale, Calif., USA). To obtain $A\beta_{1-42}$ oligomer solutions, we used a previously described protocol that results in solutions containing stable oligomers, but not fibrils for several days (Necula et al. (2007)). The lyophilized peptide was dissolved in 1 volume of 1 mM NaOH and then diluted in phosphate-buffered saline (PBS) pH 7.4 to the desired concentrations.

Aβ toxicity assay. For the Aβ neurotoxicity assay, after 7 days in vitro (DIV) the conditioned media of cortical cells was replaced with Neurobasal E medium, supplemented with 2% B27 without antioxidants (B27-AO; Invitrogen, Carlsbad, Calif.) for 2 h. Cells were then exposed to freshly prepared Aβ$_{1-42}$ solution in the presence or absence of various concentrations of cotinine.

Cell viability assays. Cell viability was quantified by MTT and propidium iodide (PI) and calcein-AM staining. MTT assay measures the viability of cells by analyzing the mitochondrial conversion of the tetrazolium salt MTT (3-(4,5-dimethylthiazol-2-yl)-2,5-diphenyl tetrazolium bromide) to formazan. To perform the MTT assay, the cell culture medium was replaced with Neurobasal medium containing freshly-dissolved MTT (0.5 mg/mL). Following 1-4 h incubation at 37° C., MTT formazan crystals were dissolved in DMSO and absorbance at 590 nm was measured. MTT results are expressed as a percentage of vehicle-treated controls.

In the double calcein-AM and Propidium iodide (PI) staining, PI binds to nucleic acid and is commonly used for identifying dead cells, since it is impermeable to the membranes of viable cells. Calcein-AM is converted to calcein by live cells, binds to the cellular calcium, and stains the cells by emitting a green fluorescence. The cortical cells were subjected to Aβ toxicity for 24 h and then 2 μM calcein-AM and 1 μM PI were added to the conditioned media and incubated for 30 min. After incubation cells were washed with PBS and the number of calcein-stained (green) and nuclei stained with PI (red) were analyzed by fluorescence microscopy. More than 600 cells per condition were analyzed in several 20× focal planes and recorded.

Western blot analysis of cell extracts. Rat embryonic cortical cells were cultured in 24-well plates (0.3×10$^6$ cells/well) for 7 days, washed with PBS, collected and disrupted by sonication in ice-cold cell lysis buffer containing (20 mM Tris (pH 7.4), 150 mM NaCl, 1 mM ethylenediaminetetraacetic acid (EDTA), 1 mM egtazic acid (EGTA), 1% triton, 2.5 mM Na pyrophosphate, 1 mM β-glycerophosphate, 1 mM Na orthovanadate, 1 μg/ml leupeptin) (Cell Signaling Technology, Beverly, Mass., USA), 1 mM phenylmethylsulfonyl fluoride (PMSF) (Sigma) complete protease inhibitor cocktail (Roche Molecular Biochemicals, Indianapolis, Ind., USA). After sonication, cell extracts were incubated on ice for 30 min and centrifuged at 20,000 g for 30 min at 4° C. Protein concentration of supernatants was measured by Bio-Rad protein assay (Bio-Rad, Hercules, Calif., USA), and equal amounts of protein were separated by gradient (4-20%) SDS-PAGE and transferred to nitrocellulose membranes (BA83 0.2 μm; Bio-Rad). The membranes were blocked in Tris-buffered saline with 0.1% Tween 20 (TTBS) containing 10% dry skim milk for 45 min. Membranes were incubated with primary antibodies in TTBS with 3% dry milk overnight at 4° C. and with secondary antibodies for 1 h. A rabbit polyclonal antibody directed against phospho-CREB kinases (Serine 133) was used (Cell Signaling). A monoclonal mouse antibody directed against β-tubulin (Promega, Madison, Wis., USA) was used to control protein sample loading and transfer efficiency. The immunoreactive bands were visualized using Dura ECL detection kit (ECL, Pharmacia Biotech, Piscataway, N.J., USA), the Kodak Image Station 440CF and analyzed using the molecular Imaging Software, version 4.0 (Rochester, N.Y., USA) and NIH ImageJ software.

Analysis of cotinine on oligomerization/aggregation of Aβ. For the analysis of the inhibition of Aβ$_{1-42}$ oligomerization/aggregation reaction, we incubated Aβ (100 μM, pH 7.4) prepared in the absence or presence of ascending concentrations of cotinine (100, 200 and 500 μM) for 7 days at 25° C. and analyzed on days 2, 5, 6 and 7. Aβ oligomerization was analyzed by Western blot and dot-blot immunoassays using antibody 6E10, which preferentially recognizes the monomeric form of Aβ and the A11 antibody that specifically recognizes the oligomeric form of the peptide but not Aβ monomers, protofibrils or fibrils.

Western blot analysis of Aβ. The western blot analysis was performed as described before (Necula et al. (2007)). 10 μl-aliquots of each oligomerization reaction containing Aβ alone or Aβ plus cotinine were mixed with 5×SDS sample buffer and loaded in a 4-20% Tris-HCl gel and analyzed by Western blot using the 6E10 antibody.

Dot-blot immunoassays. The dot-blot analysis was performed as described (Necula et al. (2007)). 4-8 μl of the oligomerization mixture was applied onto nitrocellulose membranes and allowed to dry, after which the membranes were blocked for 1 h at room temperature with 10% skim milk in TBS containing 0.05% Tween 20 (TBS-T). The membranes were then washed and incubated with 6E10 antibody (1:20,000) diluted in TBS-T containing 5% milk overnight at 4° C. After being washed with TBS-T, membranes were incubated with horseradish peroxidase-conjugated secondary antibody (1:5000) for 1 h, and visualized using enhanced chemiluminescence (Dura ECL detection kit, Pharmacia Biotech, Piscataway, N.J., USA), scanned on the Kodak Image Station 440CF, and analyzed using Molecular Imaging Software version 4.0 (Rochester, N.Y., USA) and NIH ImageJ software. The Aβ solutions for each particular day were analyzed in the same membrane and developed simultaneously.

Peptides and preparation of diffraction samples. Solutions of Aβ$_{1-42}$ were prepared by dissolving the peptide in 1 mM NaOH. Then, sufficient PBS pH 7.4 was added to make Aβ$_{1-42}$ solutions at 200 μM. These solutions were further diluted with PBS alone or PBS plus cotinine to obtain solutions with a final concentration of 100 μM Aβ and ascending concentrations of cotinine. After preparation the solutions were immediately lyophilized or incubated at room temperature (25° C.) for 3 days before lyophilization. The lyophilized samples were placed in siliconized 0.7 mm-diameter, thin-walled glass capillary tubes and kept at room temperature (RT). After x-ray diffraction the lyophilized samples were vapor-hydrated and re-examined by diffraction. The x-ray diffraction measurements were undertaken as previously detailed (Kirschner et al. (2008)).

Atomic Force Microscopy Analysis.

a) Formation of Aβ aggregates: Since the aggregation behavior of Aβ is dependent on the presence of small concentrations of aggregated forms of the peptide, that are present in many commercial samples, we prepared the Aβ solution by first dissolving the peptide in Hexafluoroisopropanol (HFIP), a protocol that produces a starting solution constituted only of Aβ monomers (Chromy et al. (2003)). Lyophillized Aβ$_{1-42}$ (American peptide) (1 mg) was dissolved in HFIP, evaporated and re-dissolved in 22 μl of dimethyl sulfoxide (DMSO, St. Louis, Mo.). These peptide preparations were then diluted in PBS buffer pH 7.4 alone or PBS plus cotinine to obtain solutions containing 1 mM Aβ$_{1-42}$ with and without 2 mM cotinine. Then the Aβ$_{1-42}$ solutions were incubated for 10 days and the formation of oligomers and fibers was examined.

b) Preparation of samples: 20 μl aliquots of Aβ solutions were deposited on freshly cleaned and dried silicon wafers (approximately 1 mm thick). After waiting for 10 mM, non-adsorbed portions of the samples were washed with de-ionized water (2000 μl). The wet surface of the silicon wafer was then dried using gentle flow of air.

c) AFM analysis: The AFM analysis was performed using an AFM apparatus (AFM, βA multimode SPM, Model no. 920-006-101, Vecco) that permits the acquisition of images using a tapping mode approach. This approach allows intermittent contact of the tip with the sample and minimizes the chances of deformation of the peptide samples. The cantilever and the tip were =made up of silicon and the cantilever force constant was approximately 20-100 N/m with the resonance frequency between 200-400 khz. The scan rate was between 1.0 to 1.2 Hz. The analysis of fibrils and oligomers was performed using the software NanoScope Control, version 5.30.

Molecular modeling. The molecular modeling of the interaction between cotinine and the $A\beta_{1-42}$ monomer was performed in the following two steps.

a) Molecular Docking: In this step, cotinine was docked near the His13 and His14 residues containing site of the full-length $A\beta_{1-42}$ peptide using the AutoDock program (version 4.0) (Morris et al. (1998)). The most representative structure obtained from our previous 50 ns MD simulations on full-length $A\beta_{1-42}$ in aqueous solution was used in the docking procedure (Triguero et al. (2008)). The reported binding sites of nicotine on $A\beta_{1-42}$ were utilized in this process (Salomon et al. (1996); Moore et al. (2004); Ono et al. (2002)). The AutoDock program performed the rapid energy evaluation through a pre-calculated grid and found the suitable binding position of cotinine on $A\beta_{1-42}$. Polar hydrogens were added using the hydrogen module in the AutoDock tools (ADT) for the peptide and the Kollman united atom partial charges were assigned. The grid was calculated using the Auto Grid protocol. It was chosen to include all the His residues (His6, His13 and His14) of $A\beta_{1-42}$. The dimension of the grid was set to 50×50×50 Å with a spacing of 0.375 Å between the two consecutive grids. In the docking process, $A\beta_{1-42}$ was kept rigid and cotinine was allowed to form all the possible torsional bonds. The AutoDock Lamarkian genetic algorithm using the standard protocol with 150 randomly placed individual initial populations was applied. In total, 50 independent docking runs were performed. The lowest energy conformer taken from the docked complex was utilized to perform 50 nanosecond (ns) MD simulations on the cotinine-$A\beta_{1-42}$ complex in aqueous solution.

b) Molecular Dynamics (MD) simulations: All molecular dynamics (MD) simulations were performed using the GROMACS software package, utilizing the GROMACS force field (Berendsen et al. (1995); Lindahl et al. (2001)). Dundee Pro Drug Server was used for generating the topology of the cotinine molecule for the MD simulation and the partial charges were also calculated using this server (Schuettelkopf and Van Aalten (2004)). The $A\beta_{1-42}$-cotinine complex was placed in the center of a box with dimensions 4.9×4.2×4.6 nm. The box contained over 2852 single point charge (SPC) water molecules. Some water molecules were replaced by sodium and chloride ions to neutralize the system and to simulate an experimentally used ion concentration of 150 mM. The starting structure was subsequently energy minimized with a steepest descent method for 2000 steps. The results of these minimizations produced the initial structure for the MD simulations. The MD simulations were then carried out with a constant number of particles (N), pressure (P) and temperature (T), i.e., NPT ensemble. The SETTLE algorithm was used to constrain the bond length and angle of the water molecules (Miyamoto and Kollman (1992)), while the LINCS algorithm was used to constrain the bond length of the peptide (Hess et al. (1997)). The long range electrostatic interactions were calculated by the particle-mesh Ewald (PME) method (Darden et al. (1993); York et al. (1994)). A constant pressure of 1 bar was applied with a coupling constant of 1.0 ps; peptide, water molecules and ions were coupled separately to a bath at 300° K. with a coupling constant of 0.1 ps. The periodic boundary conditions (PBC) were applied and the equation of motion was integrated at time-steps of 2 femtoseconds (fs). The secondary structure analyses were performed by employing the defined secondary structures of proteins (DSSP) protocol (Kabsch and Sander (1983)). The contact maps and similarity factor of the most representative structures obtained from a cluster analysis have also been employed as structural descriptors. A contact for a pair of amino acid side chains is considered to be formed when a minimal distance between any pair of their atoms is less than 0.5 nm. In the cluster analysis, the trajectories are analyzed by grouping structurally similar frames (root-mean-square-deviation (RMSD) cutoff=0.30 nm) (Daura et al. (1999)), and the frame with the largest number of neighbors is denoted as a "middle" structure, which represents that particular cluster.

Example 8—Cotinine is Neuroprotective Against Aβ Toxicity

To investigate the effect of cotinine on Aβ neurotoxicity, rat cortical cells were grown in conditions that permitted us to obtain a neuron-enriched culture (around 95% neuron and 5% glial cells) for 7-10 days. After this time, cortical cells that under microscopic examination did not show signs of neurodegeneration, were incubated in Neurobasal/B27-AO alone (control cells), and containing 5 μM Aβ, or 5 μM Aβ plus various concentrations of cotinine. After 24 h, cell survival was assessed by using MTT and PI and calcein-AM cell viability assays.

Figure 7A:
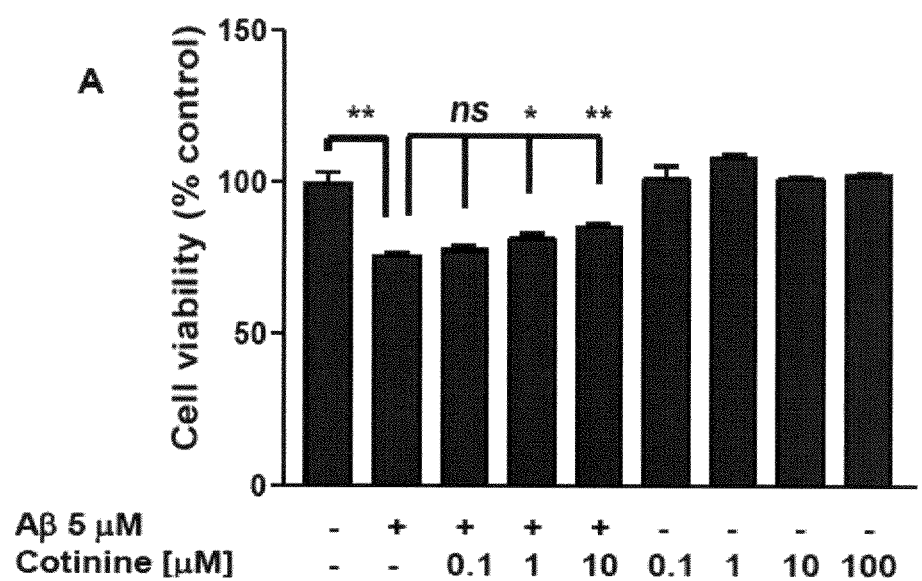

We found that cotinine added together with Aβ to the culture media, at concentrations as low as 1 μM, protected the cortical cells against Aβ toxicity. MTT assay results show that cotinine increased cell survival at doses as low as 1 μM. Maximal protection was attained with cotinine 10 μM that increased cell survival from 76% (Aβ alone) to 85% (Aβ+10 μM cotinine) of vehicle-treated control cells (FIG. 7A). These differences were statistically significant (Student's t test, Aβ+10 μM cotinine p=0.003) and representative of more than three similar experiments.

Similar results were obtained when the cell viability changes were tested using PI and calcein-AM assay. FIG. 7B shows that cotinine increased neuronal survival after Aβ exposure expressed as more green fluorescent cells and decreased the number of nuclei of degenerating brain cells that were stained by PI (red). Cotinine (10 μM) protected cortical neurons against Aβ toxicity and increased cell survival from 63% (5 μM Aβ alone) to 83% (5 μM Aβ+10 μM cotinine) of vehicle-treated control cells. This difference was statistically significant (Student's t test, p=0.0007).

Example 9—Cotinine Prevented the Formation of Toxic Forms of Aβ

Effect of Cotinine on Aβ Aggregation

Previous evidence has suggested that cotinine inhibits Aβ aggregation into fibrils (Salomon et al. (1996)). Considering the relevance in Aβ neurotoxicity of the pre-fibrillar, oligomeric and protofibrillar forms of the peptide, we investigated the effect of cotinine on Aβ aggregation into oligomers, protofibrils and fibrils.

The changes in monomer and oligomer concentrations were monitored by Western blot and dot-blot immunoassays analysis, and fibril formation was assessed by Atomic force microscopy (AFM) and X-ray microscopy.

For the analysis of Aβ oligomerization, we used a protocol that favors Aβ oligomerization over fibrillation and consists of dissolving the $Aβ_{1-42}$ peptide in sodium hydroxide and further diluting the solution with PBS as described in Experimental Procedures. Previously, It has been reported that under similar conditions of aggregation Aβ fibers did not appear before 6 days of incubation at RT (25° C.), making the oligomeric forms predominant in the solution in the absence of inhibitors (Necula et al. (2007)). Consistent with this idea, the X-ray diffraction analysis of these solutions confirmed the virtual absence of fibrils in the lyophilized samples and after vapor-hydration, after 7 days of incubation at RT (Dr. Kirchner personal communication).

Figure 8A:
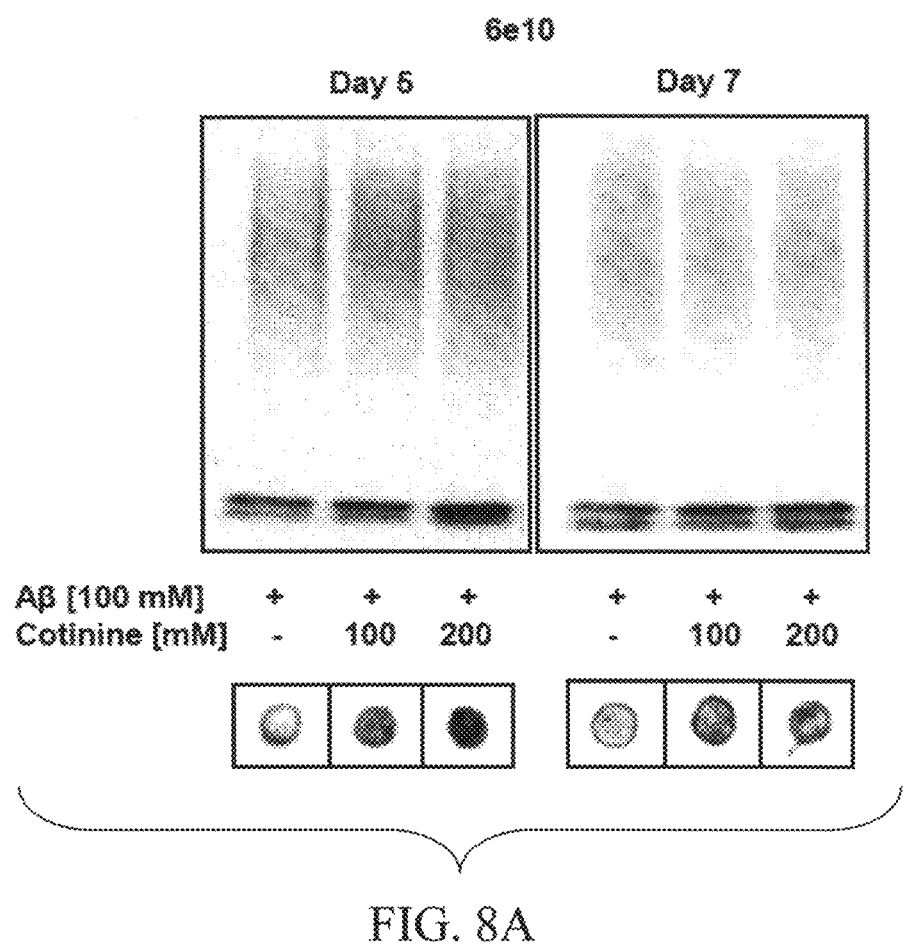
FIGS. 8A-8C. Cotinine inhibits Aβ oligomerization. 100 μM $A\beta_{1-42}$ was subjected to oligomerization conditions in the presence or absence of cotinine (100, 200, and 500 μM) for 1-7 days at room temperature and aliquots were analyzed using the anti-Aβ antibody 6E10 by Western blot and dot-blot immunoassays after 5 and 7 days (FIG. 8A) and by dot-blot immunoassays using 6E10 and the highly specific anti-Aβ antibody A11, after 2 and 6 days of incubation at RT (FIG. 8B). The results clearly show that cotinine inhibits Aβ oligomerization as expressed as a decrease in the immuno-reactivity for the A11 antibody and an increase in the immunoreactivity for the 6E10 antibody.

After an oligomerization step at 25° C. for 7 days, the Aβ solutions were analyzed by Western blot and dot-blot immunoassays using 6E10 and A11 antibodies. The Western blot analysis showed that co-incubation with ascending concentrations of cotinine increased the levels of Aβ monomers in the solutions after 5 and 7 days of incubation. Dot-blot immunoassays were also performed on days 5 and 7 to further illustrate the trend observed in the Western blots (FIG. 8A).

The subsequent analysis of the same Aβ solutions on days 2 and 6 incubated at RT by dot-blot immunoassays using the same 6E10 antibody, showed that Aβ pre-incubated with increasing concentrations of cotinine showed higher immunoreactivity for the 6E10 antibody (FIG. 8B), which in these conditions of fibrillation, and in the use of a dot-blot immunoassays, recognizes preferentially the monomeric form of the peptide.

Figure 8B:
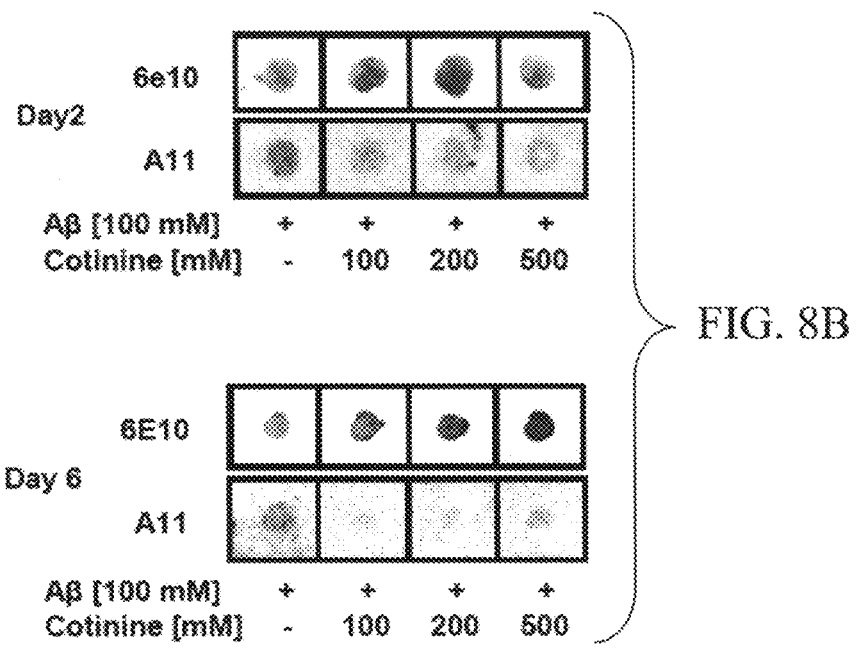
Figure 8C:
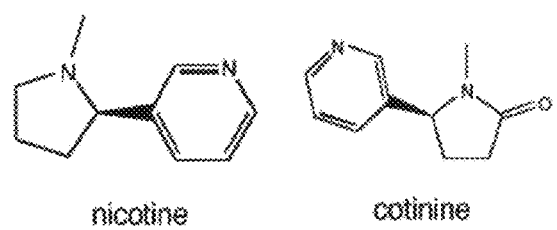

To investigate whether the increase in the 6E10 immunoreactivity in the presence of cotinine was due to a decrease in the Aβ oligomerization, we also investigated the same solutions for the presence of Aβ oligomers by dot-blot immunoassays with the anti-oligorneric Aβ antibody A11. This antibody is highly specific for the oligomeric forms of Aβ and does not recognize the monomeric or fibrillar forms of the peptide (Necula et al. (2007)). The results, from three independent experiments for any condition, showed that the presence of cotinine in the Aβ solutions decreased the concentration of Aβ oligomers expressed as a decrease in the immunoreactivity for the A11 antibody. The decrease in Aβ oligomers positively correlated with an increase in the concentration of cotinine in the samples (FIG. 8B).

Example 10—Analysis of Aβ Aggregation Using Atomic Force Microscopy

To investigate whether cotinine in addition to Aβ oligomerization also affected fibril formation, we used Atomic force miscroscopy (AFM) to analyze Aβ aggregation. The solutions were prepared dissolving Aβ in HFIP and after evaporation, in PBS alone or containing cotinine and incubated at 37° C. for 3 and 10 days.

Figures 9A, 9B, 9D, 9E:
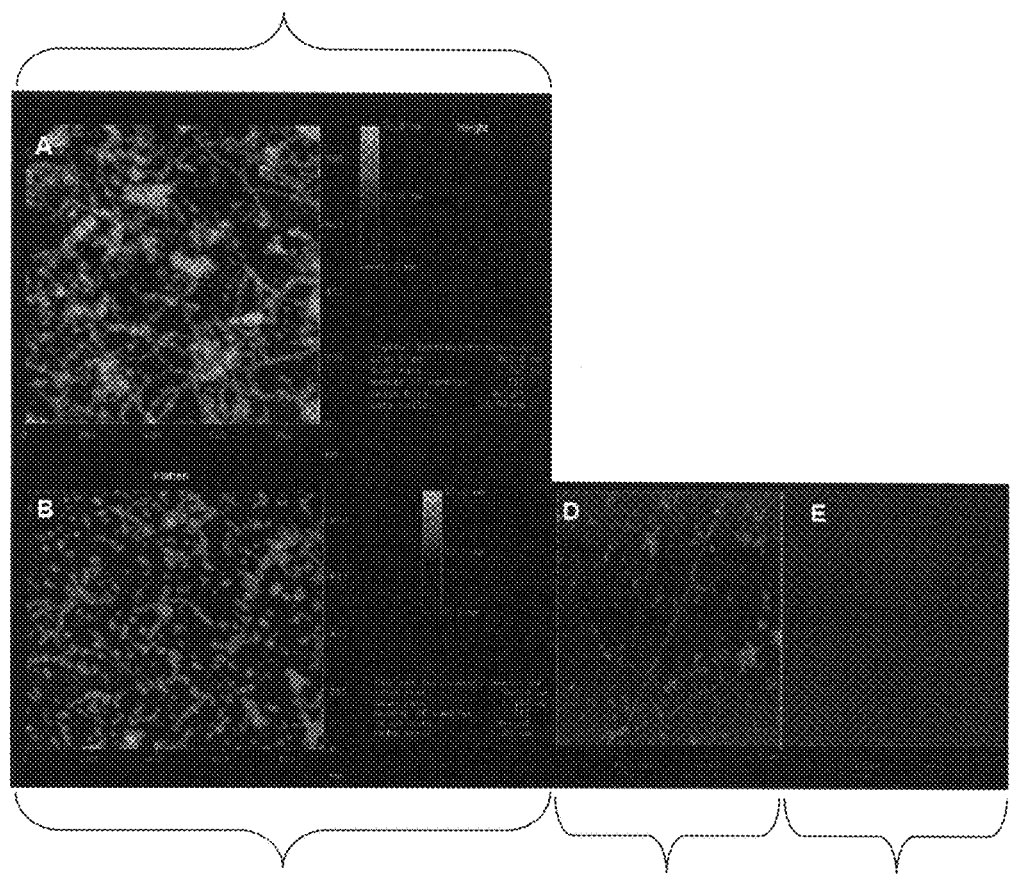
FIGS. 9A-9E. AFM analysis of the effect of cotinine on $A\beta_{1-42}$ fibrillation. A 900 nm field of $A\beta_{1-42}$ peptide incubated at concentration 1 mM for 10 days at 37° C. in the absence (FIG. 9A) or presence (FIG. 9B) of cotinine 2 mM. The plot represents the length of the Aβ fibrils formed under the conditions illustrated in FIGS. 9A and 9B. The difference in length of the $A\beta_{1-42}$ fibrils was considered significant with P=0.0228 (Student-t test) (FIG. 9C).
Figure 9C:
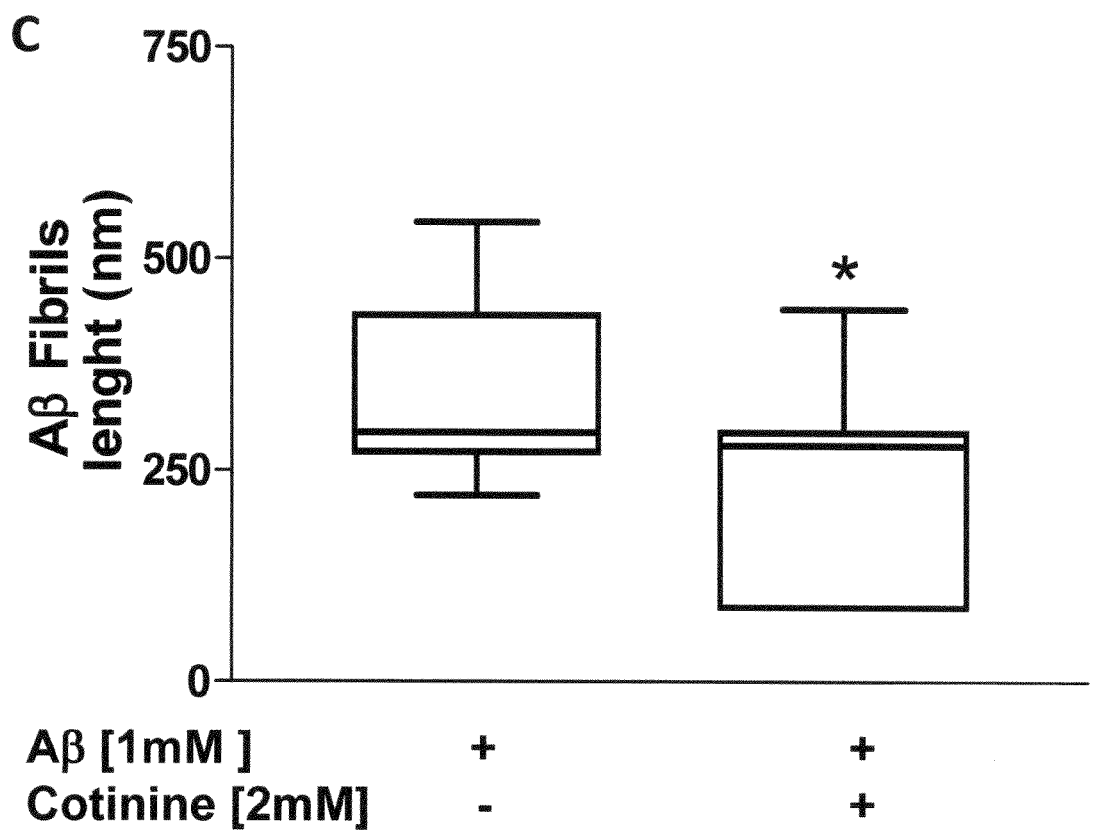

FIGS. 9A-9E present AFM images (900×900 nm field) of oligomers and fibrils of Aβ formed after incubation in either the absence (FIG. 9A and FIG. 9D) or presence cotinine (FIG. 9B) for 10 days. The analysis of Aβ fibril formation in the presence of cotinine showed that cotinine reduced Aβ aggregation and the length of Aβ fibrils. The average length of Aβ fibrils incubated in the absence of cotinine (345±42, n=8) was higher than the average fibril length in the presence of cotinine (223±36, n=23). The difference in Aβ fibril length was statistically significant when analyzed using Student-t test (p=0.0228). FIG. 9D shows the longest fibril observed in the absence of cotinine, with a length of 1.75 μm and a diameter of 34.3 nm. FIG. 9E represents the image obtained in a control experiment with PBS alone. Under our experimental conditions, the average diameter of the fibers did not change due to the presence of cotinine, and fluctuated between 22-24 nm. The average height of the aggregates fluctuated between 15-25 nm.

Example 11—Effect of Cotinine on Aβ Toxicity

Figure 10:
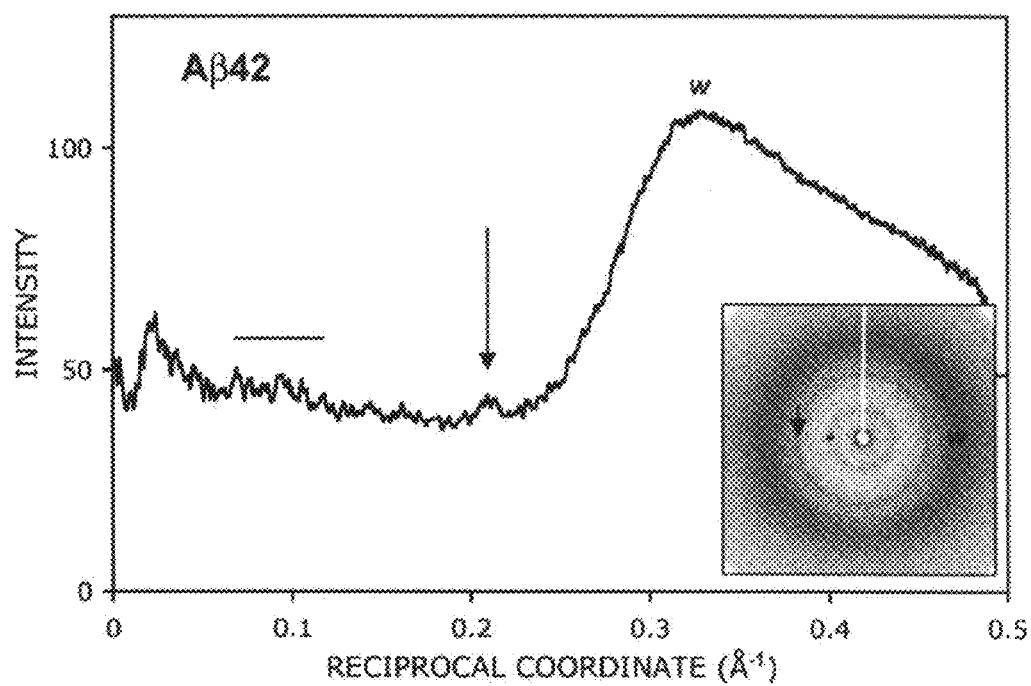
FIG. 10. x-ray analysis of the $A\beta_{1-42}$ after vapor-hydration of the lyophilized peptide. Intensity of x-ray scatter as a function of distance from the center of the pattern. Weak reflections, characteristics of β-sheet structure, are apparent at ~0.10 $\text{Å}^{-1}$ and 0.21 $\text{Å}^{-1}$, which correspond to the inter-sheet (horizontal bar) and hydrogen-bonding (arrow) reflections. The intense, broad band at 0.30-0.35 $\text{Å}^{-1}$ (w) is from water in the vapor-hydrated, lyophilized peptide. Inset, after 10 days incubation, a vapor-hydrated, lyophilized $A\beta_{1-42}$ solution shows more intense spacing from the β-conformation, suggesting the formation of more aggregates.

First, we performed x-ray analysis to investigate the presence of $Aβ_{1-42}$ fibrils in our solutions prepared using conditions that favor the oligomerization of the peptide and incubated for 3 days at 25° C. The x-ray analysis of lyophilized $Aβ_{1-42}$ before incubation showed scatter only from buffer salts (data not shown). The absence of x-ray spacing from any β-conformation indicates that the initial peptide was unstructured. After vapor-hydration of the lyophilized peptide solution that had been incubated for 3 days at RT, we detected only very weak reflections indicative of β-sheet conformation (FIG. 10). Considerably longer incubation results in more pronounced spacing from β-structure (FIG. 10, inset).

Figures 11B, 11D:
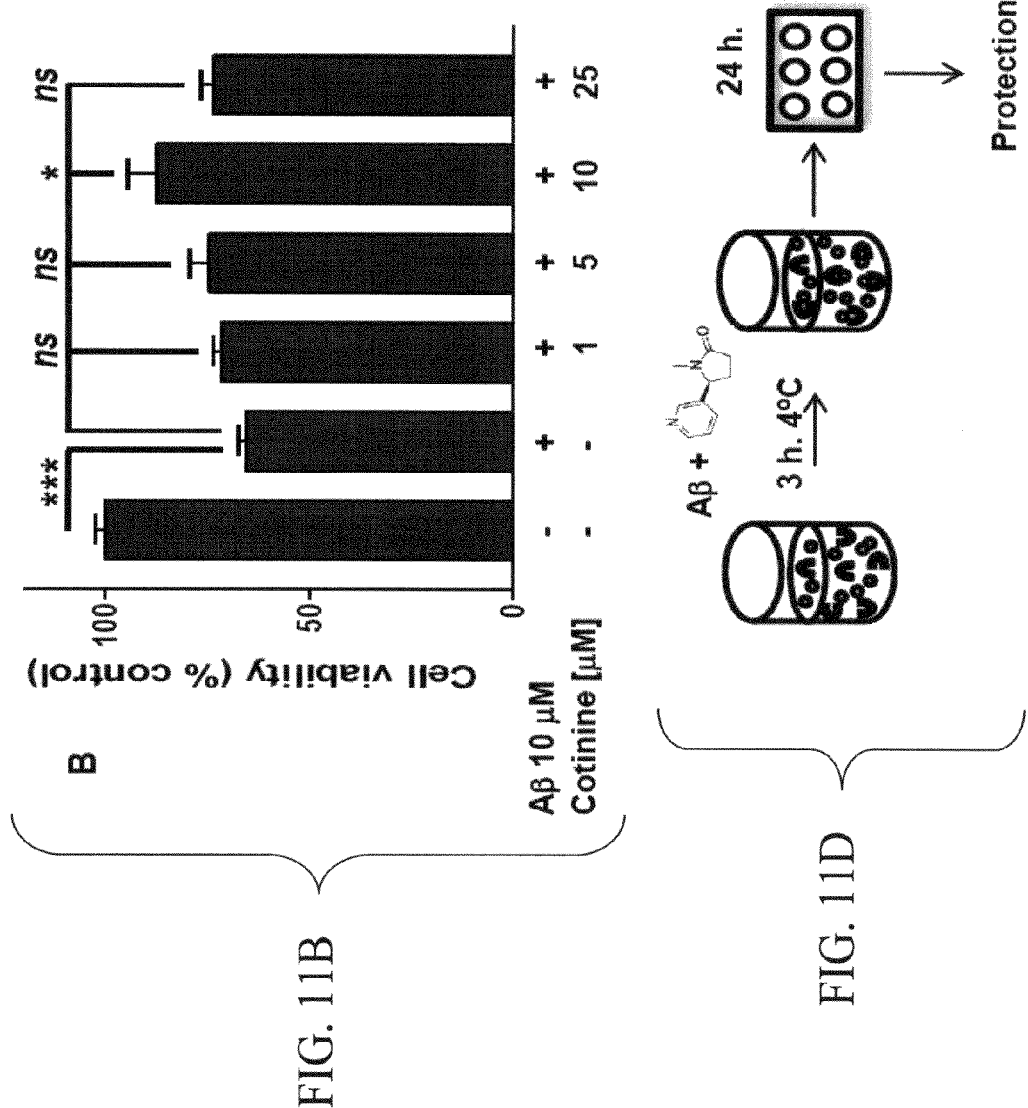

To investigate whether the inhibition of Aβ oligomerization induced by cotinine affected Aβ toxicity, we performed toxicity assays using solutions prepared by pre-incubating the peptide in the presence or absence of ascending concentrations of cotinine under conditions that favor Aβ oligomerization for 3 h at 4° C. and cell viability was assessed by using the MTT assays described in the Materials and Methods section. The results show that when the Aβ solutions were pre-incubated in the absence of cotinine, and then added to the cells, the further addition of cotinine to the culture media was not able to block Aβ neurotoxicity (FIG. 11A). However, when Aβ was dissolved and incubated in the presence of ascending concentrations of cotinine (1, 5, 10, and 25 μM), the procedure significantly reduced Aβ neurotoxicity (FIG. 11B). We found that maximal protection was attained by pre-incubating 10 μM Aβ in the presence of 10 μM cotinine. Cortical cells treated with Aβ plus cotinine (10 μM) had higher viability (87.3%±12.4) than cells treated with Aβ alone (66%±3.6) (22% increase). This increase in cell viability induced by cotinine was significant (Student's t test, P=0.019). Similar results were obtained in at least two experiments performed in identical conditions, but run with different batches of cortical cells. Taken together, this analysis suggests that the appearance of aggregated toxic forms of Aβ start to develop as early as after 3 h of incubation at temperatures as low as 4° C., and that cotinine effectively inhibited the conversion of the peptide to its toxic forms.

Example 12—Effect of Cotinine on Cell Signaling Involved in Neuronal Survival

Figures 12A, 12B:
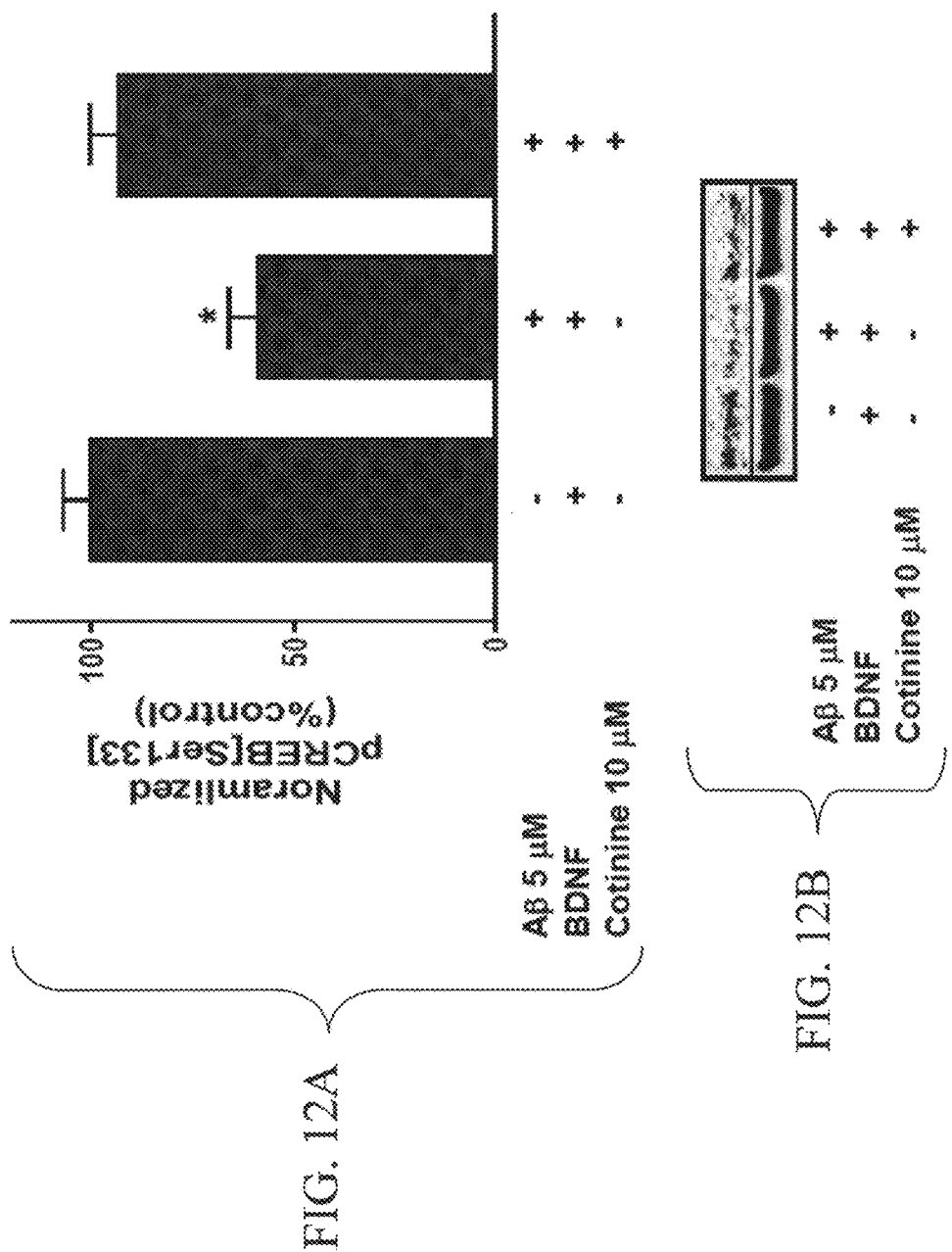
FIGS. 12A and 12B. Cotinine upregulates the levels of BDNF-stimulated phospho-CREB in cortical cells. 7 DIV cortical cells were treated with vehicle, 5 μM Aβ in the presence or absence of cotinine (10 μM) for 5 h and then treated with 100 nM BDNF for 1 h.

BDNF is a pro-survival neurotrophic factor that promotes neuronal survival and stimulates synaptic plasticity involved in learning and memory and is affected in AD (Ferrer et al. (1999); Tong et al. (2004)). To determine whether cotinine positively affects the BDNF-stimulated CREB phosphorylation after Aβ exposure, cells were incubated with 5 μM $Aβ_{1-42}$ alone or 5 μM $Aβ_{1-42}$+10 μM cotinine for 5 h. After this time, cells were stimulated with BDNF for 1 h and whole cell extracts were analyzed for the expression of CREB phosphorylated at serine 133 by western blot. We found that cotinine suppressed the Aβ-dependent inhibition of the BDNF-stimulated CREB phosphorylation at Serine 133 (FIG. 12). The levels of phosphoCREB in the $Aβ_{1-42}$ treated cells were significantly lower (41% decrease, ±10) than the levels found in the control cells considered 100% imunoreactivity (±10) (One-way ANOVA, P<0.05). Cotinine treatment significantly increased these levels to values indistinguishable from the control cell values, and significantly higher (34% increase) than the expression found in cells treated with BDNF plus $A\beta_{1-42}$ (One-way ANOVA, P<0.05).

Example 13—Molecular Modeling of Cotinine-Aβ Interaction

Figure 13:
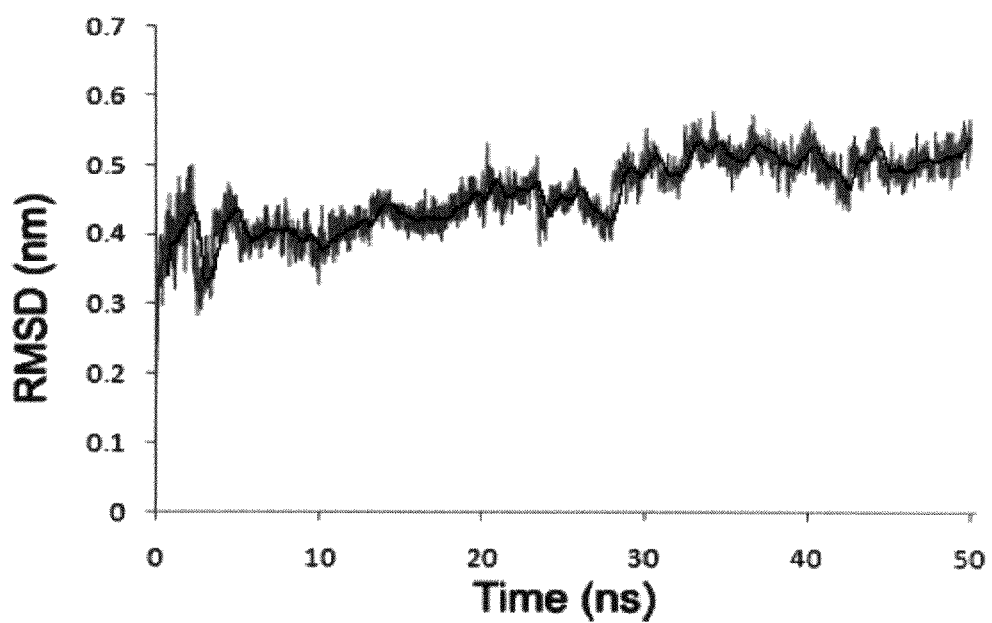
FIG. 13. Root Mean Square Deviations (RMSD) plotted against time for the molecular dynamics (MD) trajectory of $A\beta_{1-42}$-cotinine complex.
Figure 14C:
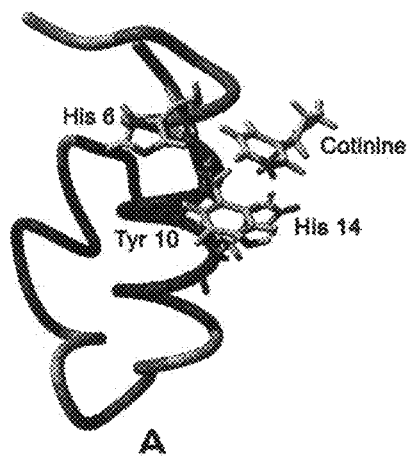
Figure 14C:
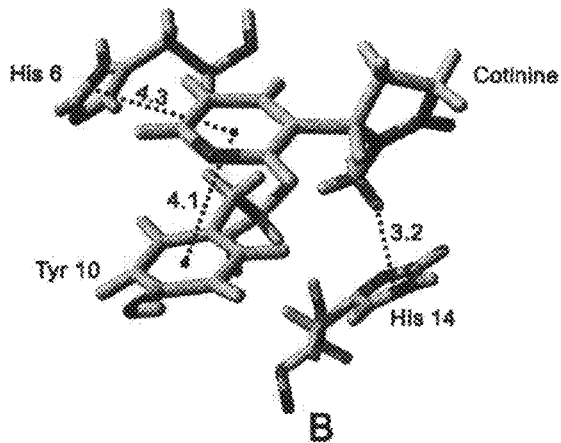
Figure 14C:
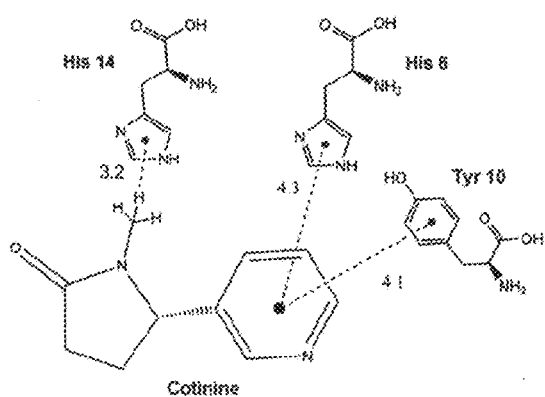
Figure 14D:
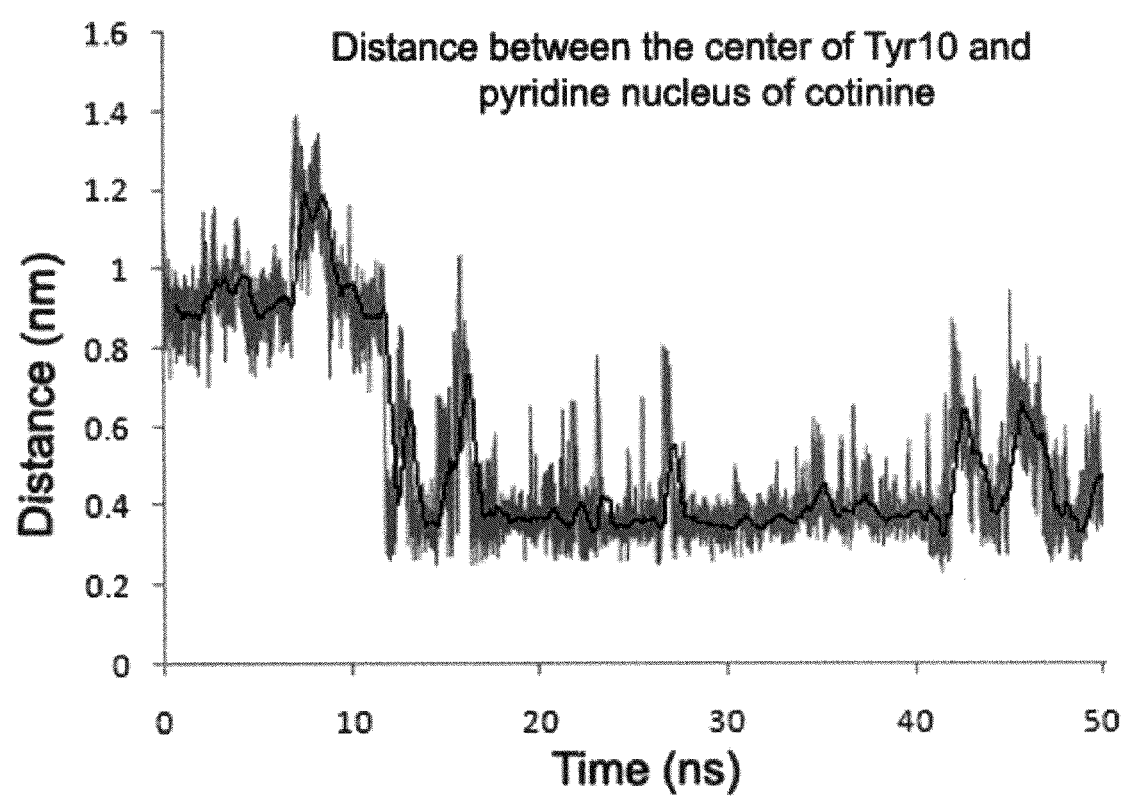

The RMSD of the MD simulation confirmed that the complex is thermodynamically equilibrated only after 30 ns (FIG. 13). The most representative structure derived from the simulation indicates that cotinine interacts with His6, Tyr10 and His14 residues of the $A\beta_{1-42}$ peptide (FIG. 14A). As shown in the figure, the pyridine ring of cotinine is positioned between the imidazole ring of His6 and the phenyl ring of Tyr10. It interacts with these residues through strong π-π interactions that are indicated by the distances of 4.3 Å and 4.1 Å between cotinine—His6 and cotinine-Tyr10 aromatic rings, respectively (FIGS. 14B and 14C). In the equilibrated region, the distance between the center of the aromatic ring of Tyr10 and the pyridine ring of cotinine remains around 4.0 Å (FIG. 14D). On the other hand, cotinine interacts with His14 via C—H-π interaction ((cotinine-C)—H-His14=3.2 Å), (FIGS. 14B and 14C). As discussed below, the interactions of cotinine with His6, Tyr10 and His14 residues of $A\beta_{1-42}$ introduce significant changes in the secondary structure of the peptide.

Figures 15A, 15B:
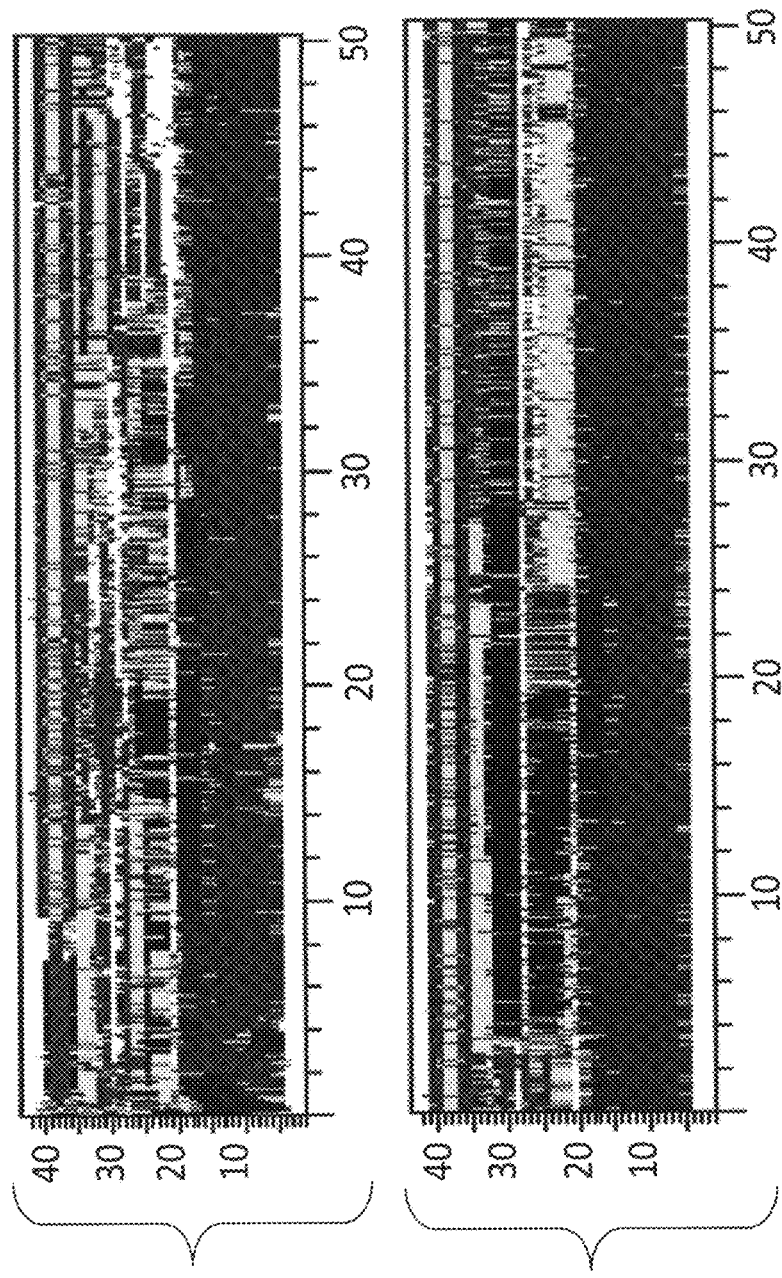
FIGS. 15A and 15B. Secondary structural assignment per residue as a function of time.

In the free $A\beta_{1-42}$ peptide, in the first 38 ns, the Phe20-Val24 region is dominated by bend and turn conformations with sporadic helical structures (FIG. 15A). After that it is transformed into bend and coil structures. However, in the cotinine bound structure, for the first 25 ns this region exists in helical conformation but it is later converted into the stable turn structure (shown by the yellow color in FIG. 15B). In the free peptide, the loop region (24-28, VGSNK) is quite unstable and undergoes a large dynamical transformation between bend and turn. In the presence of cotinine, in a marked difference, initially (for the first 22 ns) this segment exists in the helical form but later it adopts stable bend and coil conformations. The second hydrophobic domain (29-35, GAIIGLM) in free $A\beta_{1-42}$ is dominated by the bend structure for the first 28 ns but after that it is converted into a turn with a partial βsheet character. On the other hand, in the cotinine bound structure, the Gly29-Ile32 fragment of this region stays in the stable helical form throughout the simulation. The remaining Leu33-Met35 segment, after 28 ns, is transformed into the stable bend conformation.

Figure 16A:
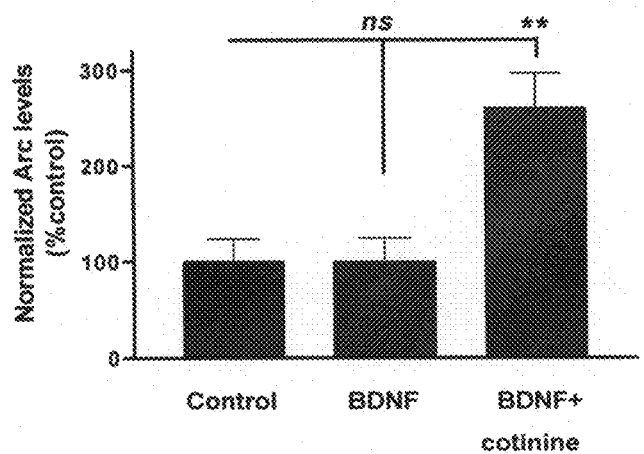
FIGS. 16A and 16B shows that cotinine stimulates BDNF-induced Arc Expression in cortical neurons. Primary cortical neurons after 7 days in vitro were stimulated with BDNF alone or BDNF plus cotinine for 2 h. Then cells were washed with PBS and disrupted by sonication in lysis buffer. Cell extracts were separated by SDS-PAGE and analyzed by Western blot with antibodies against Arc and β-tubulin, which was used as a control (FIG. 16B). The histogram represents the mean±SEM of experiments performed in triplicate. Significance of the differences were evaluated using Student's t test **highly significant (p<0.01). BDNF, brain-derived neurotrophic factor.
Figure 16B:
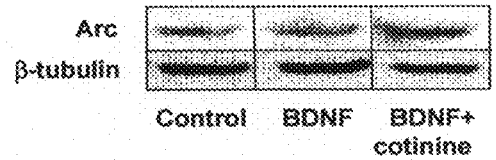

Example 14—Cotinine Stimulated BDNF-Induced Arc Expression in Primary Cortical Neurons The BDNF-stimulated expression of Arc plays a key role in learning and memory. Interestingly, it has been recently reported that Arc expression is upregulated in the hippocampus of rodents with decreased retention of fear memories. Our results show that cotinine enhances the BDNF-induced expression of Arc in cultured cortical neurons (FIGS. 16A-16B). We hypothesize that if cotinine increases the neuronal expression of Arc in vitro, it can also have the potential to decrease the retention of fear memories in vivo.

We also determined the effect of cotinine on the neuronal expression of two protein kinases, Jun kinase (JNK) and the extracellular regulated kinase (ERK1/2), which negatively and positively, respectively, regulate neuronal survival.

We found that cotinine decreased the levels of the active forms of JNK1/2 phosphorylated (pJNK) at Thr183 and Thr185, that were induced by BDNF (FIGS. 17A-17D). Since JNK promotes cell death, this decrease is coherent with the cotinine-induced reduction of neuronal cell death after Aβ exposure. The actions of cotinine seems to be mediated by defined cell signaling mechanisms different from that of nicotine as cotinine did not affect the BDNF-stimulated phosphorylation of ERK, a well known target of nicotine activation of nicotinic acetylcholine receptors (nAChR).

Example 15—Cotinine Decreased the Retention of Fear Memories

To study the effect of cotinine on contextual fear memory, we pretreated mice with vehicle or cotinine at 1 and 5 mg/kg/day for 8 days. After this time, mice were trained for contextual fear conditioning (FC). Briefly, mice were trained to associate the context (the chamber) with an aversive unconditioned stimulus (1 mA foot shock for 2 seconds). After the FC training, the mice were re-exposed to the context every day for 7 consecutive days. The mice were treated daily with vehicle or cotinine at 1 and 5 mg/kg during the FC training and re-exposure to the context. The fear memory of the mice expressed as freezing behavior was assessed each day after re-exposure to the context. The fear memory after 24 h of the FC training is considered a measure of retention of the fear memory. The reduction of fear memory expressed as a reduction in the freezing behavior after the retention trial is evaluated as the extinction of the fear memory.

The results show that cotinine treatment decreases the retention and promotes the extinction of fear memories expressed as a decrease in the freezing behavior in the retention test and in the last day of the memory extinction test (FIG. 18). The lower dose of cotinine (1 mg/kg) was more effective in decreasing the freezing behavior in the retention test. Thus, mice treated with 1 mg/kg/day of cotinine showed a significantly lower percentage of freezing (Student's t test, p=0.0191) compared to mice treated with vehicle. However, higher doses of cotinine (5 mg/kg/day) were more effective at increasing the extinction of the fear memory. Thus, mice treated with cotinine at 5 mg/kg showed a significantly lower percentage of freezing compared to mice treated with vehicle (Student's t test, p=0.0218). The changes observed in the retention test in the mice pretreated with cotinine can reflect changes in the acquisition, consolidation, and recall of the fear memory. Additional experiments will be required to determine these possibilities. However, the decrease in the freezing behavior in mice treated with cotinine 5 mg/kg at day 6 suggests that cotinine facilitates the extinction of fear memory in these mice.

Example 16—Effect of Cotinine on Anxiety as Evaluated Using the Elevated Plus Maze The elevated plus maze (EPM) is considered the first choice test for screening anxiolytic effects of drugs. This test is based on the fact that higher anxiety levels will decrease the drive to explore a new environment as a way to avoid a potentially dangerous areas (open arms), and will, therefore, cause the mice to stay immobile in the closed arms for a longer period of time.

Example 17—Effect of Cotinine on Anxiety in a Fear-Provoking Environment

To determine the effect of cotinine on anxiety, mice were tested for anxiety behavior using the EPM. The results showed that cotinine did not change the time spent exploring the maze (FIG. 19A, One-way ANOVA, $F(2,21)=0.1250$, $p=0.8831$), neither the time spent on both open (FIG. 19B, One-way ANOVA, $F(2,21)=0.8367$, $p=0.4471$) and closed arms (FIG. 19C, One-way ANOVA, $F(2,21)=0.4914$, $p=0.6186$). These results suggest that cotinine does not affect anxiety levels in mice under resting conditions.

Example 18—Effect of Cotinine on Fear-Induced Anxiety

To determine the effect of cotinine treatment on the levels of anxiety in the mice after re-exposure to a fear memory, we performed the same EPM test but 24 h after fear conditioning training (shock in the chamber) and immediately after re-exposure to the context (chamber), a reminder of the unconditioned aversive stimulus (the electric shock).

Figure 20A:
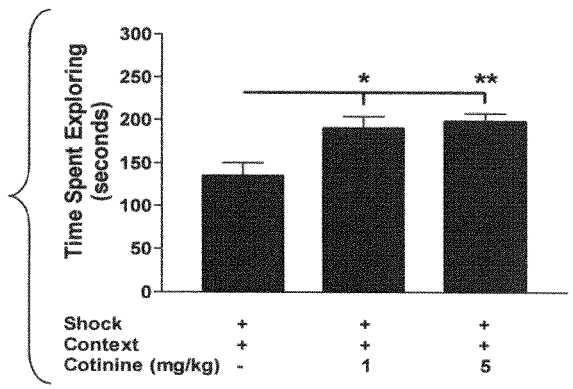
FIGS. 20A-20C show that cotinine decreased fear-induced anxiety in the elevated plus maze. Mice were trained for FC. After the retention test, the mice were tested for anxiety levels in the EPM. The number of entries into the open and closed arms and the exploratory behavior of the mice were determined using a video tracking software that measures movement in each section of the EPM. Statistical significance of the differences between groups was evaluated using One-way ANOVA with Tukey posttest. ns, not significant, * significant, P<0.05, ** highly significant P<0.01.
Figure 20B:
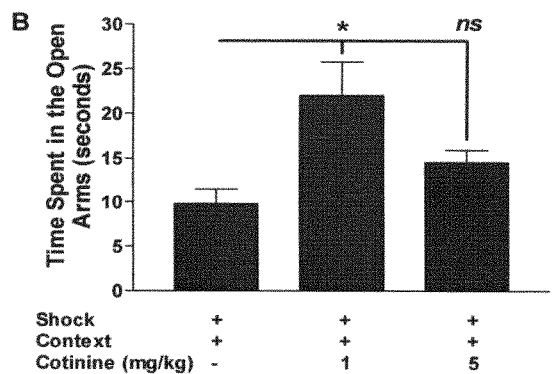
Figure 20C:
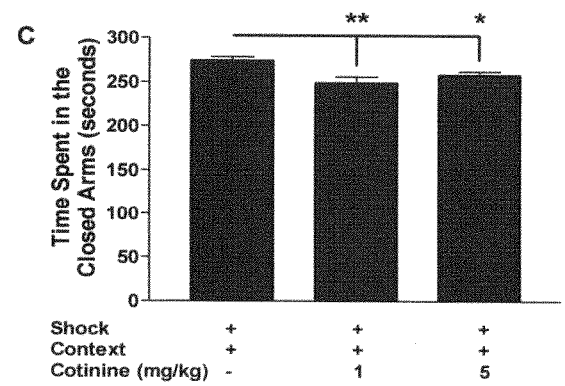
Figure 21:
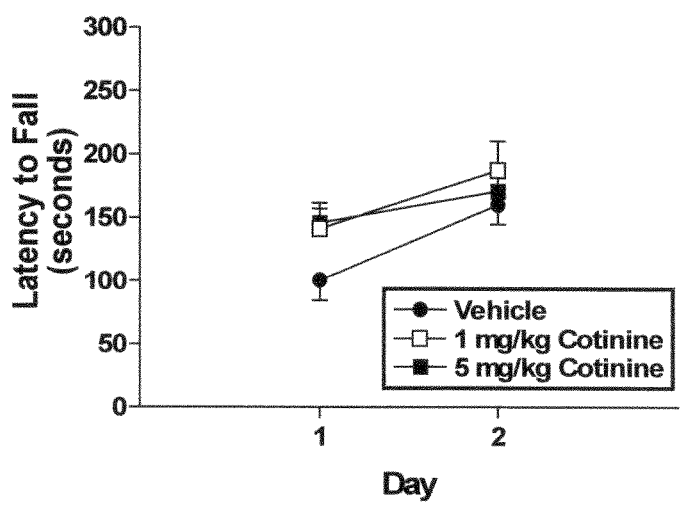
FIG. 21 shows that treatment of mice with cotinine for two weeks did not affect their sensorimotor abilities. At the end of the behavioral testing for FC, mice treated for two weeks with vehicle, cotinine 1 mg/kg and 5 mg/kg were tested in the rotarod as follows. The rotarod test was performed in an apparatus consisting of a 3 cm in diameter rod that was started at 4 rpm, accelerating up to 40 rpm for 5 min. Mice were tested for the time spent on the rod during each trial for a total of four trails per day. Testing during each trial was finished when the mouse fell off the rod and onto a spring-cushioned lever. The results are expressed as latency to fall in seconds (time spent on the rod) with 8 mice/group/treatment.
Figures 22A, 22B:
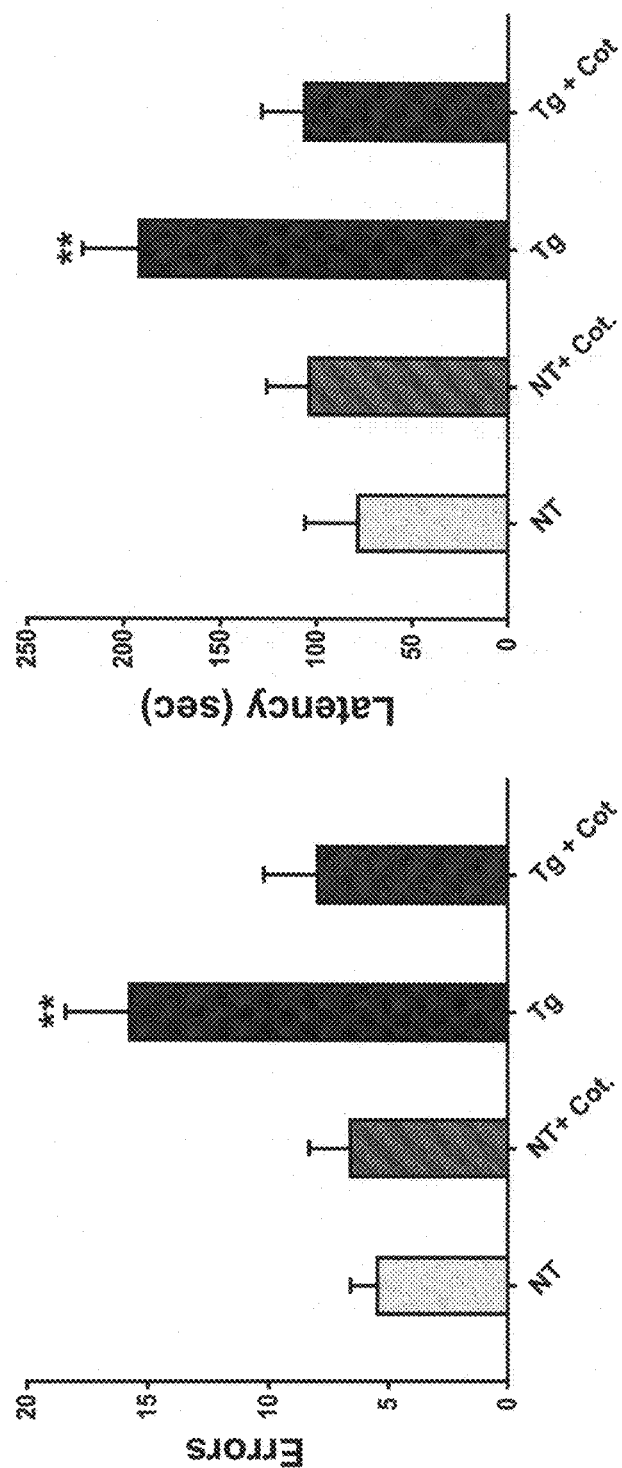
FIGS. 22A and 22B show that cotinine prevents the loss of reference memory in the circular platform. Mice of 2.5 months of age were treated or not with cotinine 2.5 mg/kg via gavage for two months and after tested in the circular platform test. In this test the number of errors to escape a 69 cm diameter circular platform containing 16 holes along its perimeter was determined in a single daily trial (300 s maximum) over 8 days of testing. Only one hole leads to an escape box, which remains the same for any given animal. To control for olfactory cures, the escape hole was relocated after each animal's trial and the maze cleaned with a dilute vinegar solution. Tg, transgenic Tg6799 mice, NT, control wild type littermate mice. N=11 mice by group.

We found significant differences between the groups in the time spent exploring (FIG. 20A, One-way ANOVA $F(2,21)=7.573$ $p=0.0033$), time spent in the open arms (FIG. 20B, One-way ANOVA $F(2,20)=5.888$ $p=0.0098$), and time spent in the closed arms (FIG. 20C, One-way ANOVA $F(2,21)=6.474$ $p=0.0065$). The mice trained for FC and treated with vehicle spent significantly less time exploring when compared with mice treated with cotinine at 1 mg/kg (FIG. 20A, Student's t test, $p=0.0145$) and 5 mg/kg ($p=0.0025$). Also, mice trained for FC and treated with vehicle spent significantly less time in the open arms than mice subjected to FC and treated with 1 mg/kg cotinine (FIG. 20B, Student's t test, $p=0.0101$) but no significant differences with mice treated with cotinine at 5 mg/kg ($p=0.0545$). In coherence with these results, mice trained for fear conditioning spent less time in the closed arms (FIG. 20C). This difference was highly significant when the untreated mice were compared to mice treated with cotinine 1 mg/kg (Student's t test, $p=0.0060$) and 5 mg/kg ($p=0.0111$).

Example 19—Effect of Cotinine on Motor Coordination in Mice

To discard a confounding effect of cotinine on learning due to changes in motor coordination and fatigue, we tested mice in the rotarod test after 2 weeks of treatment with vehicle or cotinine at the doses indicated in the figure below.

The analysis of the results shows that the differences in latency between groups to fall on the first and second day were not significant. Two weeks of cotinine treatment did not affect sensorimotor abilities in the mice. Similar to this test, no changes in sensorimotor abilities were detected by using the open field activity test (data not shown).

Example 20

It has been discovered using cultured cortical neurons that cotinine inhibits Aβ oligomerization in vitro and prevents its toxicity on cortical neurons. Studies performed in vitro have shown that cotinine binds to Aβ with high affinity. Cotinine can also bind Aβ in vivo with high affinity and consequently, when labeled for detection by Positron Emission tomography, it can be used as a diagnostic tool to determine the presence of senile plaques in the brain of AD patients.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,938,949
Berendsen H J C, van der Spoel, D., and van Drunen, D (1995) GROMACS: A message-passing parallel molecular dynamics implementation. *Computer Physics Communications* 91, 43-56.
Birtwistle J, Hall K (1996) Does nicotine have beneficial effects in the treatment of certain diseases? *Br J Nurs* 5, 1195-1202.
Boscarino, J E (2006). Posttraumatic stress disorder and mortality among U.S. Army veterans 30 years after military service. *Ann Epidemiol* 16 (4)248-56.
Brewer G J (1995) Serum-free B27/neurobasal medium supports differentiated growth of neurons from the striatum, substantia nigra, septum, cerebral cortex, cerebellum, and dentate gyms. *J Neurosci Res* 42, 674-683.
Briggs C A, McKenna D G, Piattoni-Kaplan M (1995) Human alpha 7 nicotinic acetylcholine receptor responses to novel ligands. *Neuropharmacology* 34, 583-590.
Buccafusco J J, Shuster L C, Terry A V, Jr. (2007) Disconnection between activation and desensitization of autonomic nicotinic receptors by nicotine and cotinine. *Neurosci Lett.* 413, 68-71.
Calhoun, Bosworth, Grambow, Dudley, & Beckham, (2002). Medical service utilization by veterans seeking help for posttraumatic stress disorder. *Am J Psychiatry*. 159 (12): 2081-6
Chromy B A, Nowak R J, Lambert M P, Viola K L, Chang L, Velasco P T, Jones B W, Fernandez S J, Lacor P N, Horowitz P, Finch C E, Krafft G A, Klein W L (2003) Self-assembly of Abeta(1-42) into globular neurotoxins. *Biochemistry* 42, 12749-12760.
Court J A, Johnson M, Religa D, Keverne J, Kalaria R, Jaros E, McKeith I G, Perry R, Naslund J, Perry E K (2005) Attenuation of Abeta deposition in the entorhinal cortex of normal elderly individuals associated with tobacco smoking. *Neuropathol Appl Neurobiol* 31, 522-535.
Darden T A, York, D., and Pedersen, L. (1993) Particle mesh Ewald: An N·log(N) method for Ewald sums in large systems. *Journal of Chemical Physics* 98, 10089-10092.
Daura X, van Gunsteren W F, Mark A E (1999) Folding-unfolding thermodynamics of a beta-heptapeptide from equilibrium simulations. *Proteins* 34, 269-280.
Doolittle D J, Winegar R, Lee C K, Caldwell W S, Hayes A W, de Bethizy J D (1995) The genotoxic potential of nicotine and its major metabolites. *Mutat Res* 344, 95-102.
Echeverria, V, Cuello, A C (2002) *Mol. Neurobiol.*, 26(2-3):299-316.
Echeverria, V. et al. (2005) *Eur. J. Neurosci*, 22:2199-2206.
Ferrer I, Marin C, Rey M J, Ribalta T, Goutan E, Blanco R, Tolosa E, Marti E (1999) BDNF and full-length and truncated TrkB expression in Alzheimer disease. Implications in therapeutic strategies. *J Neuropathol Exp Neurol* 58, 729-739.

Gahring L C, Meyer E L, Rogers S W (2003) Nicotine-induced neuroprotection against N-methyl-D-aspartic acid or beta-amyloid peptide occur through independent mechanisms distinguished by pro-inflammatory cytokines. *J Neurochem* 87, 1125-1136.

Gallinat J, Meisenzahl E, Jacobsen L K, Kalus P, Bierbrauer J, Kienast T, Witthaus H, Leopold K, Seifert F, Schubert F, Staedtgen M (2006) Smoking and structural brain deficits: a volumetric MR investigation. *Eur J Neurosci* 24, 1744-1750.

Hammond D K, Bjercke R J, Langone J J, Strobel H W (1991) Metabolism of nicotine by rat liver cytochromes P-450. Assessment utilizing monoclonal antibodies to nicotine and cotinine. *Drug Metab Dispos* 19, 804-808.

Hellstrom-Lindahl E, Court J, Keverne J, Svedberg M, Lee M, Marutle A, Thomas A, Perry E, Bednar I, Nordberg A (2004) Nicotine reduces A beta in the brain and cerebral vessels of APPsw mice. *Eur J Neurosci* 19, 2703-2710.

Hess B, Bekker, H., Berendsen, H. J. C., and Fraaije, J. G. E. M (1997) LINCS: A linear constraint solver for molecular simulations. *Journal of Computational Chemistry* 18, 1463-1472.

Hoge, C W et al., 2004, *N Eng J Med,* 351:13-22.

Hong D P, Fink A L, Uversky V N (2009) Smoking and Parkinson's disease: does nicotine affect alpha-synuclein fibrillation? *Biochim Biophys Acta* 1794, 282-290.

Hsiao K, Chapman P, Nilsen S, Eckman C, Harigaya Y, Younkin S, Yang F, Cole G (1996) Correlative memory deficits, Abeta elevation, and amyloid plaques in transgenic mice. *Science* 274, 99-102.

Kabsch W, Sander C (1983) Dictionary of protein secondary structure: pattern recognition of hydrogen-bonded and geometrical features. *Biopolymers* 22, 2577-2637.

Kessler (2000). Posttraumatic stress disorder: the burden to the individual and to society. *J Clin Psychiatr.* 61 Suppl 5 4-12; discussion 13-4

Kessler et al., 2005, *Arch. Gen. Psychiatry,* 62:617-627.

Kessler, Sonnega, Bromet, Hughes, & Nelson, 1995, Posttraumatic stress disorder in the National Comorbidity Survey. *Arch. Gen. Psychiatry,* 52:1048-1060.

Kirschner D A, Gross A A, Hidalgo M M, Inouye H, Gleason K A, Abdelsayed G A, Castillo G M, Snow A D, Pozo-Ramajo A, Petty S A, Decatur S M (2008) Fiber diffraction as a screen for amyloid inhibitors. *Curr Alzheimer Res* 5, 288-307.

Kudo, Y., Okamura, N., Furumoto, S., Tashiro, M., Furukawa, K. et al. (2007) "2-(2-[2-Dimethylaminothiazol-5-yl]ethenyl)-6-(2-[fluoro]ethoxy)benzoxazole: a novel PET agent for in vivo detection of dense amyloid plaques in Alzheimer's disease patients" *J. Nucl. Med.,* 48:553-561.

Levin E D (2002) Nicotinic receptor subtypes and cognitive function. *J Neurobiol* 53, 633-640.

Lindahl E, Hess, B., and van der Spoel, D. (2001) GROMACS 3.0: a package for molecular simulation and trajectory analysis. 7, 306-317.

Merchant C, Tang M X, Albert S, Manly J, Stern Y, Mayeux R (1999) The influence of smoking on the risk of Alzheimer's disease. *Neurology* 52, 1408-1412.

Miyamoto S, and Kollman, P. A (1992) SETTLE: An analytical version of the SHAKE and RATTLE algorithms for rigid water models. *Journal of Computational Chemistry* 13, 952-962.

Moore S A, Huckerby T N, Gibson G L, Fullwood N J, Turnbull S, Tabner B J, El-Agnaf O M, Allsop D (2004) Both the D-(+) and L-(−) enantiomers of nicotine inhibit Abeta aggregation and cytotoxicity. *Biochemistry* 43, 819-826.

Morris G M, Goodsell, D. S., Halliday, R. S., Huey, R., Hart, W. E., Belew, R. K. and Olson, A. J. (1998) Automated Docking Using a Lamarckian Genetic Algorithm and and Empirical Binding Free Energy Function. *Journal of Computational Chemistry* 19, 1639-1662.

Necula M, Kayed R, Milton S, Glabe C G (2007) Small molecule inhibitors of aggregation indicate that amyloid beta oligomerization and fibrillization pathways are independent and distinct. *J Biol Chem* 282, 10311-10324.

Nordberg A, Hellstrom-Lindahl E, Lee M, Johnson M, Mousavi M, Hall R, Perry E, Bednar I, Court J (2002) Chronic nicotine treatment reduces beta-amyloidosis in the brain of a mouse model of Alzheimer's disease (APPsw). *J Neurochem* 81, 655-658.

Oddo S, Caccamo A, Green K N, Liang K, Tran L, Chen Y, Leslie F M, LaFerla F M (2005) Chronic nicotine administration exacerbates tau pathology in a transgenic model of Alzheimer's disease. *Proc Natl Acad Sci USA* 102, 3046-3051.

Ono K, Hasegawa K, Yamada M, Naiki H (2002) Nicotine breaks down preformed Alzheimer's beta-amyloid fibrils in vitro. *Biol Psychiatry* 52, 880-886.

Solomon S D & Davidson, (1997). Trauma: prevalence, impairment, service use, and cost. *J Clin Psychiatry.* 58 Suppl 9. 5-11.

Salomon A R, Marcinowski K J, Friedland R P, Zagorski M G (1996) Nicotine inhibits amyloid formation by the beta-peptide. *Biochemistry* 35, 13568-13578.

Schnurr & Jankowski, (1999). Physical health and post-traumatic stress disorder: review and synthesis. *Semin Clin Neuropsychiatry* 4(4):295-304.

Schuettelkopf A. W. and Van Aalten DMF (2004) PRODRG—a tool for high-throughput crystallography of protein-ligand complexes. *Acta Crystallographica* 60, 1355-1363.

Szymanska I, Radecka H, Radecki J, Kaliszan R (2007) Electrochemical impedance spectroscopy for study of amyloid beta-peptide interactions with (−) nicotine ditartrate and (−) cotinine. *Biosens Bioelectron* 22, 1955-1960.

Terry A V, Jr., Hernandez C M, Hohnadel E J, Bouchard K P, Buccafusco J J (2005) Cotinine, a neuroactive metabolite of nicotine: potential for treating disorders of impaired cognition. *CNS Drug Rev* 11, 229-252.

Tong L, Balazs R, Thornton P L, Cotman C W (2004) Beta-amyloid peptide at sublethal concentrations down-regulates brain-derived neurotrophic factor functions in cultured cortical neurons. *J Neurosci* 24, 6799-6809.

Triguero L, Singh R, Prabhakar R (2008) Comparative molecular dynamics studies of wild-type and oxidized forms of full-length Alzheimer amyloid beta-peptides Abeta(1-40) and Abeta(1-42). *J Phys Chem B* 112, 7123-7131.

Unger C, Hedberg M M, Mustafiz T, Svedberg M M, Nordberg A (2005) Early changes in Abeta levels in the brain of APPswe transgenic mice—implication on synaptic density, alpha7 neuronal nicotinic acetylcholine- and N-methyl-D-aspartate receptor levels. *Mol Cell Neurosci* 30, 218-227.

Yolton K, Dietrich K, Auinger P, Lanphear B P, Hornung R (2005) Exposure to environmental tobacco smoke and cognitive abilities among U.S. children and adolescents. *Environ Health Perspect* 113, 98-103.

York D M, Wlodawer A, Pedersen L G, Darden T A (1994) Atomic-level accuracy in simulations of large protein crystals. *Proc Natl Acad Sci USA* 91, 8715-8718.

I claim:

1. A method for treating a post-traumatic stress disorder or condition, said method comprising administering an amount of cotinine, or a composition comprising cotinine to a person or animal in an effective amount in order to enhance the extinction of fear memory in a person or animal in need of treatment and thereby treating the subject with the PTSD or condition.

* * * * *